US009845329B2

United States Patent
Uno et al.

(10) Patent No.: US 9,845,329 B2
(45) Date of Patent: Dec. 19, 2017

(54) METHOD FOR PRODUCING A SUBSTITUTED 6,7,8,9-TETRAHYDROPYRIMIDO [5,4-B]INDOLIZINE, SUBSTITUTED 7,8,9,10-TETRAHYDRO-6H-PYRIMIDO [5',4':4,5]PYRROLO[1,2-A]AZEPINE AND SUBSTITUTED 6,7,8,9,10,11-HEXAHYDROPYRIMIDO[5',4':4,5]PYRROLO [1,2-A]AZOCINE

(71) Applicant: TAIHO PHARMACEUTICAL CO., LTD., Tokyo (JP)

(72) Inventors: Takao Uno, Tsukuba (JP); Tadashi Shimamura, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/760,296

(22) PCT Filed: Feb. 21, 2014

(86) PCT No.: PCT/JP2014/054218
§ 371 (c)(1),
(2) Date: Jul. 10, 2015

(87) PCT Pub. No.: WO2014/129596
PCT Pub. Date: Aug. 28, 2014

(65) Prior Publication Data
US 2016/0115172 A1    Apr. 28, 2016

(30) Foreign Application Priority Data

Feb. 22, 2013  (JP) .................................. 2013-033886
Feb. 22, 2013  (TW) ............................. 102106272 A
Feb. 22, 2013  (WO) ................. PCT/JP2013/054615
Aug. 16, 2013  (JP) .................................. 2013-169200

(51) Int. Cl.
C07D 487/14    (2006.01)
C07F 7/18       (2006.01)
C07D 471/14    (2006.01)
C07D 487/04    (2006.01)

(52) U.S. Cl.
CPC ......... *C07D 487/14* (2013.01); *C07D 471/14* (2013.01); *C07D 487/04* (2013.01); *C07F 7/1852* (2013.01)

(58) Field of Classification Search
CPC .................................................. C07D 487/14
USPC ....................................................... 544/252
See application file for complete search history.

(56) References Cited

U.S. PATENT DOCUMENTS

2014/0057899 A1* 2/2014 Sagara .................. C07D 487/14
514/214.02

FOREIGN PATENT DOCUMENTS

| CN | 101175755 A | 5/2008 |
|----|-------------|--------|
| CN | 101610676 A | 12/2009 |
| CN | 101674834 A | 3/2010 |
| CN | 102146059 A | 8/2011 |
| TW | 201204364 A1 | 2/2012 |
| TW | 201305118 A1 | 2/2013 |
| WO | 2006/102079 A1 | 9/2006 |
| WO | 2007/075554 A2 | 7/2007 |
| WO | 2007114926 A2 | 10/2007 |
| WO | 2008018881 A1 | 2/2008 |
| WO | 2008039218 A2 | 4/2008 |
| WO | 2008121742 A2 | 10/2008 |
| WO | 2011/046964 A2 | 4/2011 |
| WO | 2011162515 A2 | 12/2011 |
| WO | 2012061299 A1 | 5/2012 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Rixson et al., "The Development of Domino Reactions Incorporating the Heck Reaction: The Formation of N-Heterocycles", The European Journal of Organic Chemistry, 2012, vol. 2012, No. 3, pp. 544-558.
Huang et al., "Synthesis of Cyclopropanes by Pd-Catalyzed Activation of Alkyl C—H Bonds", Tetrahedron Letters, 2009, vol. 50, No. 52, pp. 7235-7238.
Jana et al., "Synthesis of Phenanthrene and Alkyl Phenanthrenes by Palladium (0)-Catalyzed Pericyclic Reactions", Synthesis, 2010, No. 12, pp. 2092-2100.
Merlic et al, "Synthesis of Indolocarbazoles via Sequential Palladium Catalyzed Cross-Coupling and Benzannulation Reactions", Tetrahedron Letters, 1997, vol. 38, No. 44, pp. 7661-7664.

(Continued)

*Primary Examiner* — Douglas M Willis
(74) *Attorney, Agent, or Firm* — Rothwell, Figg, Ernst & Manbeck, P.C.

(57) ABSTRACT

A method for producing a pyrrolopyrimidine ring-containing tricyclic compound represented by Formula (1)

(1)

or a salt thereof. The method comprising the steps of: (I) reacting an organoborane reagent with a compound represented by Formula (2) or a salt thereof, and (II) performing an intramolecular cyclization reaction of the reaction product of step (I) in the presence of a zerovalent palladium catalyst and an alkali metal hydroxide.

7 Claims, No Drawings

(56) References Cited

OTHER PUBLICATIONS

Harrison et al., "Novel Class of LIM-Kinase 2 Inhibitors for the Treatment of Ocular Hypertension and Associated Glaucoma", Journal of Medicinal Chemistry, 2009, vol. 52, No. 21, pp. 6515-6518.

Freeman-Cook et al, "Design of Selective, ATP-Competitive Inhibitors of Akt", Journal of Medicinal Chemistry, 2010, vol. 53, No. 12, pp. 4615-4622.

Translation of Chemical Innovative Experiments, 2012, 8 pages.

\* cited by examiner

METHOD FOR PRODUCING A SUBSTITUTED 6,7,8,9-TETRAHYDROPYRIMIDO [5,4-B]INDOLIZINE, SUBSTITUTED 7,8,9,10-TETRAHYDRO-6H-PYRIMIDO[5',4':4,5] PYRROLO[1,2-A]AZEPINE AND SUBSTITUTED 6,7,8,9,10,11-HEXAHYDROPYRIMIDO[5',4':4,5]PYRROLO [1,2-A]AZOCINE

TECHNICAL FIELD

CROSS REFERENCE OF RELATED APPLICATIONS

This application is a 35 U.S.C. 371 National Phase Entry Application from PCT/JP2014/054218, filed Feb. 21, 2014, which claims the benefit of Japanese Patent Application No. 2013-033886 filed on Feb. 22, 2013; PCT/JP2013/054615 filed Feb. 22, 2013; Taiwan Patent Application No. 102106272 filed Feb. 22, 2013; and Japanese Patent Application No. 2013-169200 filed Aug. 16, 2013, the disclosures of which are incorporated herein in their entirety by reference.

The present invention relates to a method for producing a pyrrolopyrimidine ring-containing tricyclic compound, and to a tricyclic compound capable of being obtained by this production method.

BACKGROUND ART

A pyrrolopyrimidine ring is known as a partial structure commonly possessed by many kinase inhibitors (Non-patent Literature (NPL) 3 and Non-patent Literature (NPL) 4).

The method disclosed in Patent Literature (PTL) 1 has been known as a method for producing a pyrrolopyrimidine ring-containing tricyclic compound.

In the method disclosed in PTL 1, an organic borane reagent is caused to act on a pyrrolopyrimidine derivative to prepare an alkyl borane intermediate in the system, and an intramolecular cyclization reaction is then performed using a divalent palladium catalyst to thereby produce a pyrrolopyrimidine ring-containing tricyclic compound. However, this method suffers from low yield, as shown in Comparative Example 1 below.

The intramolecular cyclization reaction using a zerovalent palladium catalyst has also been known (Non-patent Literature (NPL) 1 and Non-patent Literature (NPL) 2).

NPL 1 reports a method that uses a zerovalent palladium catalyst and cesium carbonate as a base. However, this method also suffers from low yield, as shown in Comparative Example 2 below.

NPL 2 reports a method that uses a zerovalent palladium catalyst and thallium carbonate as a base. However, thallium carbonate is an acute toxic substance and is not preferably used in a production method.

CITATION LIST

Patent Literature

PTL 1: WO 2006/102079

Non-patent Literature

NPL 1: Synthesis 2010, No. 127, 2092-2100
NPL 2: Tetrahedron 1997, 38, 7661-7664
NPL 3: J. Med. Chem. 2009, 52, 6515-6518
NPL 4: J. Med. Chem. 2010, 53, 4615-4622

SUMMARY OF INVENTION

Technical Problem

An object of the present invention is to provide a method for reproducibly producing a pyrrolopyrimidine ring-containing tricyclic compound in high yield with reduced formation of by-products, and to provide a novel tricyclic compound.

Solution to Problem

The present inventors conducted extensive research to achieve the above object, and found that a combined use of a zerovalent palladium catalyst and an alkali metal hydroxide enables the production of a pyrrolopyrimidine ring-containing tricyclic compound in high yield with high reproducibility, with reduced formation of by-products. The present invention has thereby been accomplished.

More specifically, the present invention provides the following method for producing a tricyclic compound, and the following tricyclic compound useful as a production intermediate of medicinal drugs and the like.

Item 1. A method for producing a compound represented by Formula (1)

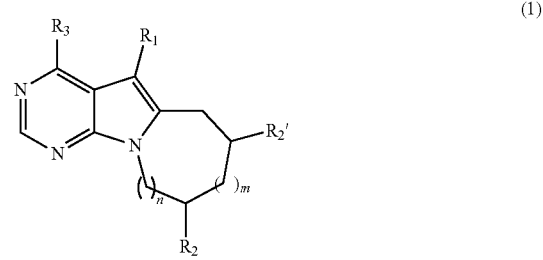

or a salt thereof,
wherein
$R_1$ is hydrogen or a functional group;
one of $R_2$ or $R_2'$ is
  hydroxyl protected by a protecting group selected from the group consisting of lower alkylsilyl, lower alkyldiphenylsilyl, lower alkyl lower alkoxyphenylsilyl, and lower alkoxydiphenylsilyl,
  amino or $C_{1-6}$ alkylamino protected by alkyloxycarbonyl which may be substituted, or
  thiol protected by a protecting group selected from the group consisting of aralkyl, benzyloxymethyl, benzylthiomethyl, lower alkoxycarbonyl, 2,2,2-trichloroethoxycarbonyl, 9-fluorenylmethoxycarbonyl, tert-butylsulfanyl, and 3-nitro-2-pyridinesulfenyl;
the other one of $R_2$ or $R_2'$ is hydrogen; and
$R_3$ is amino which may be substituted;
m is an integer of 0 to 2; and
n is an integer of 0 or more and such that 0≤m+n≤3,
the method comprising the steps of:
  (I) causing an organic borane reagent to act on a compound represented by Formula (2)

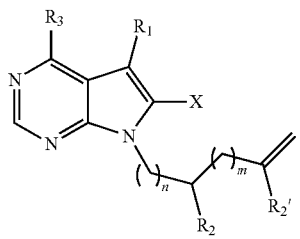

(2)

or a salt thereof,
wherein X is halogen, and $R_1$, $R_2$, $R_2'$, $R_3$, m, and n are as defined above; and (II) performing an intramolecular cyclization reaction of the reaction product obtained in step (I) above, using a zerovalent palladium catalyst in the presence of an alkali metal hydroxide.

Item 2. The production method according to Item 1, wherein the zerovalent palladium catalyst is tetrakis(triphenylphosphine)palladium(0) or tris(dibenzylideneacetone)dipalladium(0).

Item 3. The production method according to Item 1 or 2, wherein the alkali metal hydroxide is lithium hydroxide, sodium hydroxide, potassium hydroxide, or cesium hydroxide.

Item 4. The production method according to any one of Items 1 to 3, wherein the organic borane reagent is 9-BBN (9-borabicyclo[3.3.1]nonane) or 9-BBN (9-borabicyclo[3.3.1]nonane) dimer.

Item 5. The production method according to any one of Items 1 to 4,
wherein
X is bromine or iodine;
$R_1$ is hydrogen, $C_{1-6}$ alkyl which may be substituted, $C_{3-10}$ cycloalkyl which may be substituted, $C_{6-14}$ aromatic hydrocarbon which may be substituted, 4- to 10-membered saturated heterocycle which may be substituted, or 4- to 10-membered unsaturated heterocycle which may be substituted;
one of $R_2$ or $R_2'$ is hydroxyl protected by a protecting group selected from the group consisting of lower alkylsilyl, lower alkyldiphenylsilyl, lower alkyl lower alkoxyphenylsilyl, and lower alkoxydiphenylsilyl, or amino or $C_{1-6}$ alkylamino protected by alkyloxycarbonyl which may be substituted;
the other one of $R_2$ or $R_2'$ is hydrogen; and
$R_3$ is amino.

Item 6. The production method according to any one of Items 1 to 5,
wherein
m and n is such that (m, n)=(0, 1), (1, 1), (0, 2), (2, 1), or (1, 2);
X is bromine or iodine;
$R_1$ is hydrogen, $C_{3-7}$ cycloalkyl, $C_{6-14}$ aromatic hydrocarbon, or 4- to 10-membered unsaturated heterocycle;
one of $R_2$ or $R_2'$ is hydroxyl protected by a protecting group selected from the group consisting of lower alkylsilyl, lower alkyldiphenylsilyl, lower alkyl lower alkoxyphenylsilyl, and lower alkoxydiphenylsilyl, or amino or $C_{1-6}$ alkylamino protected by alkyloxycarbonyl which may be substituted;
the other one of $R_2$ or $R_2'$ is hydrogen; and
$R_3$ is amino.

Item 7. The production method according to any one of Items 1 to 6,
wherein
m and n is such that (m, n)=(0, 1), (1, 1), or (0, 2);
X is bromine or iodine;
$R_1$ is hydrogen, cyclopropyl, phenyl, or quinolyl;
one of $R_2$ or $R_2'$ is hydroxyl protected by tert-butyldimethylsilyl, or amino or $C_{1-4}$ alkylamino protected by tert-butoxycarbonyl, and the other one of $R_2$ or $R_2'$ is hydrogen; and
$R_3$ is amino.

Item 8. A compound represented by Formula (1')

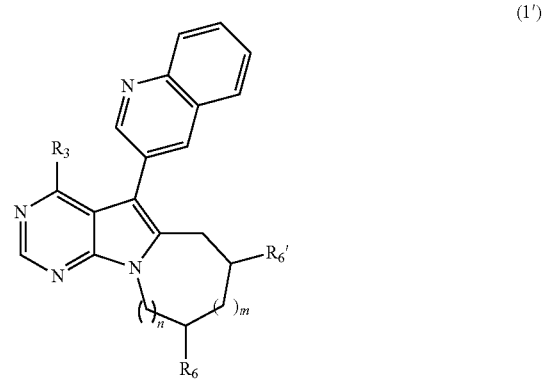

(1')

or a salt thereof,
wherein m is an integer of 0 to 2;
n is an integer of 0 or more and such that $0 \le m+n \le 3$;
$R_3$ is amino which may be substituted;
one of $R_6$ or $R_6'$ is amino or $C_{1-6}$ alkylamino protected by alkyloxycarbonyl which may be substituted; and
the other one of $R_6$ or $R_6'$ is hydrogen.

Item 9. The compound or a salt thereof according to Item 8,
wherein
m and n is such that (m, n)=(0, 1), (1, 1), (0, 2), (2, 1), or (1, 2);
$R_3$ is amino;
one of $R_6$ or $R_6'$ is amino or $C_{1-6}$ alkylamino protected by alkyloxycarbonyl which may be substituted; and
the other one of $R_6$ or $R_6'$ is hydrogen.

Item 10. The compound or a salt thereof according to Item 8 or 9,
wherein
m and n is such that (m, n)=(0, 1), (1, 1), or (0, 2);
$R_3$ is amino;
one of $R_6$ or $R_6'$ is amino or $C_{1-4}$ alkylamino protected by tert-butoxycarbonyl;
and the other one of $R_6$ or $R_6'$ is hydrogen.

Advantageous Effects of Invention

The production method of the present invention reproducibly produces a pyrrolopyrimidine ring-containing tricyclic compound in high yield with reduced formation of by-products, and is thus suitable for industrial production.

The tricyclic compound produced by the production method of the present invention is very useful as a production intermediate of medicinal drugs and the like.

DESCRIPTION OF EMBODIMENTS

The following describes embodiments of the present invention. However, the present invention is not limited to these embodiments.

The present invention provides a method for producing a compound represented by Formula (1) above or a salt thereof, the method comprising the steps of:
(I) causing an organic borane reagent to act on a compound represented by Formula (2) or a salt thereof; and
(II) performing an intramolecular cyclization reaction of the reaction product obtained in step (I) above, using a zerovalent palladium catalyst in the presence of an alkali metal hydroxide.

The letter m in the formulae represents an integer of 0 to 2, and is preferably 0 or 1.

The letter n in the formulae represents an integer that satisfies $0 \leq m+n \leq 3$, and is preferably 1 or 2.

A combination of m and n is preferably such that (m, n)=(0, 1), (1, 1), (0, 2), (2, 1), or (1, 2), and more preferably (m, n)=(0, 1), (1, 1), or (0, 2).

In this specification, the functional group represented by $R_1$ may be any group as long as the production method of the present invention proceeds. Specific examples include halogen, hydroxyl, cyano, nitro, alkyl which may be substituted, haloalkyl which may be substituted, cycloalkyl which may be substituted, cycloalkyl-alkyl which may be substituted, aralkyl which may be substituted, alkenyl which may be substituted, alkynyl which may be substituted, alkoxy which may be substituted, haloalkoxy which may be substituted, cycloalkoxy which may be substituted, cycloalkyl-alkoxy which may be substituted, aralkyloxy which may be substituted, alkylthio which may be substituted, cycloalkyl-alkylthio which may be substituted, amino which may be substituted, alkylamino which may be substituted, cycloalkyl-alkylamino which may be substituted, acyl which may be substituted, acyloxy which may be substituted, oxo, carboxyl which may be substituted, alkoxycarbonyl which may be substituted, aralkyloxycarbonyl which may be substituted, carbamoyl which may be substituted, saturated or unsaturated heterocycle, aromatic hydrocarbon, saturated heterocyclic oxy, and other groups. In the present invention, hydrogen is not included in the functional groups.

In addition to the groups listed above, the functional group represented by $R_1$ also includes the groups listed above that are protected by protecting groups.

In the present specification, when a group is "protected," it means that a protecting group has been introduced into the group so that the group does not adversely affect the production method of the present invention. The protecting groups are not limited insofar as they can protect the groups mentioned above. Examples of usable protecting groups include those listed below as protecting groups for protected hydroxyl, protected amino, protected $C_{1-6}$ alkylamino, and protected thiol.

Examples of halogen as used herein include fluorine, chlorine, bromine, iodine, and the like, unless otherwise defined.

Alkyl as used herein may be straight chain or branched chain, and may be, for example, $C_{1-6}$ alkyl. $C_{1-6}$ alkyl refers to $C_{1-6}$ straight or branched alkyl, such as methyl, ethyl, n-propyl, isopropyl, n-butyl, isobutyl, sec-butyl, tert-butyl, n-pentyl, isopentyl, and hexyl, unless otherwise defined.

Haloalkyl as used herein refers to a group in which from one to all of the hydrogen atoms in the alkyl mentioned above are replaced by the halogen mentioned above. Examples include a group in which from one to all of the hydrogen atoms of the $C_{1-6}$ alkyl mentioned above are replaced by the halogen mentioned above ($C_{1-6}$ haloalkyl). Examples of $C_{1-6}$ haloalkyl include monofluoromethyl, difluoromethyl, trifluoromethyl, 1-fluoroethyl, 2-fluoroethyl, 1,1-difluoroethyl, 1,2-difluoroethyl, 2,2-difluoroethyl, 3-chloropropyl, 4-chlorobutyl, 5-fluoropentyl, 6-fluorohexyl, and the like. It is preferable to use $C_{1-4}$ haloalkyl, such as monofluoromethyl, difluoromethyl, trifluoromethyl, trichloromethyl, fluoroethyl, 1,1,1-trifluoroethyl, monofluoro-n-propyl, perfluoro-n-propyl, perfluoroisopropyl, 3-chloropropyl, and 4-fluorobutyl.

Cycloalkyl as used herein refers to monocyclic or polycyclic alkyl, such as $C_{3-10}$ cycloalkyl. $C_{3-10}$ cycloalkyl refers to $C_{3-10}$ monocyclic or polycyclic alkyl, such as cyclopropyl, cyclobutyl, cyclopentyl, cyclohexyl, cycloheptyl, and decalyl, unless otherwise defined. Further, $C_{3-7}$ cycloalkyl refers to $C_{3-7}$ monocyclic or polycyclic alkyl, such as cyclopropyl, cyclobutyl, cyclopentyl, cyclohexyl, and cycloheptyl, unless otherwise defined.

Examples of cycloalkyl-alkyl as used herein include $C_{1-4}$ alkyl substituted with $C_{3-7}$ cycloalkyl, such as cyclopropylmethyl, cyclobutylmethyl, cyclopentylmethyl, cyclohexylmethyl, and cycloheptylmethyl.

Examples of aralkyl as used herein include $C_{7-13}$ aralkyl, such as benzyl, phenethyl, naphthylmethyl, and fluorenylmethyl.

Alkenyl as used herein may be straight, branched, or cyclic, and refers to an unsaturated hydrocarbon group having at least one double bond. Examples include $C_{2-6}$ alkenyl, such as vinyl, allyl, 1-propenyl, 2-methyl-2-propenyl, isopropenyl, 1-, 2-, or 3-butenyl, 2-, 3-, or 4-pentenyl, 2-methyl-2-butenyl, 3-methyl-2-butenyl, 5-hexenyl, 1-cyclopentenyl, 1-cyclohexenyl, and 3-methyl-3-butenyl; and the like.

Alkynyl as used herein may be straight, branched, or cyclic, and refers to an unsaturated hydrocarbon group having at least one triple bond. Examples include $C_{2-6}$ alkynyl, such as ethynyl, 1- or 2-propynyl, 1-, 2-, or 3-butynyl, and 1-methyl-2-propynyl; and the like.

Alkoxy as used herein may be straight or branched alkoxy. Examples include $C_{1-6}$ alkoxy. $C_{1-6}$ alkoxy refers to $C_{1-6}$ straight or branched alkoxy, such as methoxy, ethoxy, n-propoxy, isopropoxy, n-butoxy, isobutoxy, tert-butoxy, pentyloxy, isopentyloxy, and hexyloxy, unless otherwise defined.

Haloalkoxy as used herein refers to $C_{1-6}$ straight or branched alkoxy containing 1 to 13 halogen atoms ("halo $C_{1-6}$ alkoxy"), and preferably halo $C_{1-4}$ alkoxy. Examples include fluoromethoxy, difluoromethoxy, trifluoromethoxy, trichloromethoxy, fluoroethoxy, 2,2,2-trifluoroethoxy, monofluoro-n-propoxy, perfluoro-n-propoxy, perfluoro-isopropoxy, 5-fluoropentyloxy, 6-fluorohexyloxy, and the like.

Examples of cycloalkoxy as used herein include $C_{3-7}$ cycloalkoxy, such as cyclopropoxy, cyclobutoxy, cyclopentyloxy, cyclohexyloxy, and cycloheptyloxy; and the like.

Examples of cycloalkyl-alkoxy as used herein include $C_{1-4}$ alkoxy substituted with $C_{3-7}$ cycloalkyl, such as cyclopropylmethoxy, cyclobutylmethoxy, cyclopentylmethoxy, cyclohexylmethoxy, and cycloheptylmethoxy; and the like.

Examples of aralkyloxy as used herein include $C_{7-13}$ aralkyloxy, such as benzyloxy, phenethyloxy, naphthylmethyloxy, and fluorenylmethyloxy; and the like.

Alkylthio as used herein may be straight or branched. Examples thereof include $C_{1-6}$ alkylthio, such as methylthio, ethylthio, n-propylthio, isopropylthio, n-butylthio, isobutylthio, tert-butylthio, n-pentylthio, isopentylthio, hexylthio; and the like.

Examples of cycloalkyl-alkylthio as used herein include $C_{1-4}$ alkylthio substituted with $C_{3-7}$ cycloalkyl, such as cyclopropylmethylthio, cyclobutylmethylthio, cyclopentylmethylthio, cyclohexylmethylthio, and cycloheptylmethylthio; and the like.

Examples of alkylamino as used herein include a group in which one or two of the hydrogen atoms of amino are replaced by the alkyl mentioned above ("monoalkylamino" or "dialkylamino"). Examples include $C_{1-6}$ alkylamino. $C_{1-6}$ alkylamino refers to amino in which one or two of the hydrogen atoms are replaced by the $C_{1-6}$ alkyl mentioned above.

Examples of monoalkylamino as used herein include amino monosubstituted with straight or branched $C_{1-6}$ alkyl, such as methylamino, ethylamino, n-propylamino, isopropylamino, n-butylamino, isobutylamino, tert-butylamino, n-pentylamino, isopentylamino, and hexylamino; and the like.

Examples of dialkylamino as used herein include amino disubstituted with straight or branched $C_{1-6}$ alkyl, such as dimethylamino, diethylamino, di-n-propylamino, diisopropylamino, di-n-butylamino, isobutylamino, di-tert-butylamino, di-n-pentylamino, diisopentylamino, dihexylamino, and ethylmethylamino; and the like.

Examples of cycloalkyl-alkylamino as used herein include $C_{1-4}$ alkylamino substituted with $C_{3-7}$ cycloalkyl, such as cyclopropylmethylamino, cyclobutylmethylamino, cyclopentylmethylamino, cyclohexylmethylamino, and cycloheptylmethylamino; and the like.

Acyl as used herein is a residue obtained by removing hydroxyl from the carboxyl group of a carboxy-containing compound, and indicates alkylcarbonyl or arylcarbonyl.

Examples of alkylcarbonyl include straight or branched ($C_{1-6}$ alkyl) carbonyl, such as methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, and hexylcarbonyl; and the like.

Examples of arylcarbonyl include ($C_{6-13}$ aryl) carbonyl, such as phenylcarbonyl, naphthylcarbonyl, fluorenylcarbonyl, anthrylcarbonyl, biphenylylcarbonyl, tetrahydronaphthylcarbonyl, chromanylcarbonyl, 2,3-dihydro-1,4-dioxanaphthalenylcarbonyl, indanylcarbonyl, and phenanthrylcarbonyl; and the like.

Acyloxy as used herein refers to alkylcarbonyloxy or arylcarbonyloxy.

Examples of alkylcarbonyloxy include straight or branched ($C_{1-6}$ alkyl) carbonyloxy, such as methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, and hexylcarbonyloxy; and the like.

Examples of arylcarbonyloxy include ($C_{6-13}$ aryl) carbonyloxy, such as phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy, and phenanthrylcarbonyloxy; and the like.

Alkoxycarbonyl as used herein refers to carbonyl to which the alkoxy mentioned above is attached, and may be straight or branched. Examples thereof include $C_{2-7}$ alkoxycarbonyl. Examples of $C_{2-7}$ alkoxycarbonyl include methoxycarbonyl, ethoxycarbonyl, n-propoxycarbonyl, isopropoxycarbonyl, n-butoxycarbonyl, isobutoxycarbonyl, hexyloxycarbonyl, and the like.

Examples of aralkyloxycarbonyl include ($C_{7-13}$ aralkyl) oxycarbonyl, such as benzyloxycarbonyl, phenethyloxycarbonyl, naphthylmethyloxycarbonyl, and fluorenylmethyloxycarbonyl; and the like.

Saturated heterocycle as used herein refers to 4- to 10-membered monocyclic or polycyclic, partially saturated or saturated heterocycle having 1 to 4 atoms selected from among oxygen, nitrogen, and sulfur, unless otherwise defined ("4- to 10-membered saturated heterocycle"). Specific examples of saturated heterocycle include pyrrolidinyl, piperidinyl, piperazinyl, hexamethyleneimino, morpholino, thiomorpholino, homopiperazinyl, tetrahydrofuranyl, tetrahydropyranyl, and the like. Examples of partially saturated heterocycle include methylenedioxyphenyl, ethylenedioxyphenyl, dihydrobenzofuranyl, oxetanyl, and the like. These are preferably monocyclic or bicyclic.

Unsaturated heterocycle as used herein refers to 4- to 10-membered monocyclic or polycyclic unsaturated heterocycle having 1 to 4 atoms selected from among oxygen, nitrogen, and sulfur ("4- to 10-membered unsaturated heterocycle"), unless otherwise defined. Specific examples include imidazolyl, thienyl, furyl, pyrrolyl, oxazolyl, isoxazolyl, thiazolyl, isothiazolyl, thiadiazolyl, pyrazolyl, triazolyl, tetrazolyl, pyridyl, pyrazinyl, pyrimidinyl, pyridazinyl, indolyl, isoindolyl, indazolyl, triazolopyridyl, benzimidazolyl, benzoxazolyl, benzothiazolyl, benzothienyl, benzofuranyl, purinyl, quinolyl, isoquinolyl, quinazolinyl, quinoxalinyl, and the like. These are preferably monocyclic or bicyclic.

Examples of aromatic hydrocarbon as used herein include phenyl, tolyl, xylyl, naphthyl, anthracenyl, phenanthryl, fluorenyl, tetrahydronaphthyl, and the like. It is preferable to use $C_{6-14}$ monocyclic or polycyclic aromatic hydrocarbon ("$C_{6-14}$ aromatic hydrocarbon"). Examples of $C_{6-14}$ aromatic hydrocarbon include phenyl, tolyl, xylyl, naphthyl, anthracenyl, phenanthryl, fluorenyl, tetrahydronaphthyl, and the like. These are preferably monocyclic or bicyclic.

Saturated heterocyclic oxy as used herein refers to oxy to which the saturated heterocycle mentioned above are attached. Examples include morpholinyloxy, 1-pyrrolidinyloxy, piperidinyloxy, piperazinyloxy, 4-methyl-1-piperazinyloxy, tetrahydrofuranyloxy, tetrahydropyranyloxy, tetrahydrothiophenyloxy, thiazolidinyloxy, oxazolidinyloxy, and the like.

The "functional group" represented by $R_1$ is preferably $C_{1-6}$ alkyl which may be substituted, $C_{3-10}$ cycloalkyl which may be substituted, $C_{6-14}$ aromatic hydrocarbon which may be substituted, 4- to 10-membered saturated heterocycle which may be substituted, or 4- to 10-membered unsaturated heterocycle which may be substituted. The "functional group" represented by $R_1$ may also be a functional group other than $C_{1-6}$ alkyl which may be substituted, $C_{3-10}$ cycloalkyl which may be substituted, $C_{6-14}$ aromatic hydrocarbon which may be substituted, 4- to 10-membered saturated heterocycle which may be substituted, and 4- to 10-membered unsaturated heterocycle which may be substituted. Examples of "$C_{1-6}$ alkyl which may be substituted, $C_{3-10}$ cycloalkyl which may be substituted, $C_{6-14}$ aromatic hydrocarbon which may be substituted, 4- to 10-membered saturated heterocycle which may be substituted, and 4- to 10-membered unsaturated heterocycle which may be substituted" include halogen, hydroxyl, cyano, nitro, alkyl having 7 or more carbon atoms (e.g., $C_{7-15}$ alkyl) which may be substituted, haloalkyl which may be substituted, cycloalkyl having 11 or more carbon atoms which may be substituted (e.g., $C_{11-15}$ cycloalkyl which may be substituted), cycloalkyl-alkyl which may be substituted, aralkyl which may be substituted, alkenyl which may be substituted, alkynyl which may be substituted, alkoxy which may be substituted, haloalkoxy which may be substituted, cycloalkoxy which may be substituted, cycloalkyl-alkoxy which may be substituted, aralkyloxy which may be substituted, alkylthio which may be substituted, cycloalkyl-alkylthio which may be substituted, amino which may be substituted, alkylamino which may be substituted, cycloalkyl-alkylamino which may be substituted, acyl which may be substituted, acyloxy which may be substituted, oxo, carboxyl which may be substituted, alkoxycarbonyl which may be substituted, aralkyloxycarbonyl which may be substituted, carbamoyl which may be substituted, 11- or more-membered saturated heterocycle which may be substituted (e.g., 11- to 15-membered saturated heterocycle which may be substituted), 11- or more-membered unsaturated heterocycle which may be substituted (e.g., 11- to 15-membered unsaturated heterocycle which may be substituted), monocyclic or polycyclic aromatic hydrocarbon having 15 or more carbon atoms which may be substituted (e.g., $C_{15-30}$ monocyclic or polycyclic aromatic hydrocarbon which may be substituted), saturated heterocyclic oxy which may be substituted, and the like.

In this specification, when $R_1$ represents a functional group, the substituents mentioned above are not limited as long as they do not adversely affect the production method of the present invention.

In this specification, substituents for $C_{1-6}$ alkyl represented by $R_1$ are not limited as long as they do not adversely affect the production method of the present invention. Examples include halogen, $C_{1-6}$ alkoxy, acyl, $C_{2-7}$ alkoxycarbonyl, $C_{1-6}$ alkylamino, $C_{3-10}$ cycloalkyl, $C_{6-14}$ aromatic hydrocarbon, 4- to 10-membered saturated heterocycle, 4- to 10-membered unsaturated heterocycle, and the like.

In this specification, substituents for $C_{3-10}$ cycloalkyl, $C_{6-14}$ aromatic hydrocarbon, 4- to 10-membered saturated heterocycle, 4- to 10-membered unsaturated heterocycle represented by $R_1$ are not limited as long as they do not adversely affect the production method of the present invention. Examples include halogen, $C_{1-6}$ alkyl, $C_{1-6}$ alkoxy, $C_{1-6}$ haloalkyl, acyl, $C_{2-7}$ alkoxycarbonyl, $C_{1-6}$ alkylamino, $C_{3-10}$ cycloalkyl, $C_{6-14}$ aromatic hydrocarbon, 4- to 10-membered saturated heterocycle, 4- to 10-membered unsaturated heterocycle, and the like.

In this specification, substituents for amino represented by $R_3$ are not limited as long as they do not adversely affect the production method of the present invention. Examples include $C_{1-6}$ alkyl, $C_{1-6}$ haloalkyl, acyl, $C_{2-7}$ alkoxycarbonyl, $C_{1-6}$ alkylamino, $C_{3-10}$ cycloalkyl, 4- to 10-membered saturated heterocycle, and the like. The substituents for amino represented by $R_3$ may include protecting groups to be removed after a predetermined reaction process, as well as substituents that are not protecting groups, as long as they do not adversely affect the production method of the present invention.

When contained, the number of substituents is typically one to three.

The halogen represented by X in the formula may be those listed above, and is preferably bromine or iodine.

$R_1$ is more preferably hydrogen, $C_{3-7}$ cycloalkyl, $C_{6-14}$ aromatic hydrocarbon, or 4- to 10-membered unsaturated heterocycle.

The "$C_{3-7}$ cycloalkyl group" represented by $R_1$ in the formulae may be, for example, those listed above, and is preferably cyclopropyl.

The "$C_{6-14}$ aromatic hydrocarbon" represented by $R_1$ in the formulae may be, for example, those listed above, and is preferably phenyl.

The "4- to 10-membered unsaturated heterocycle" represented by $R_1$ in the formulae may be, for example, those listed above. It is preferable to use 4- to 10-membered monocyclic or bicyclic unsaturated heterocycle having 1 to 4 atoms selected from among oxygen, nitrogen, and sulfur. It is more preferable to use monocyclic or bicyclic unsaturated heterocycle containing at least one nitrogen atom in the ring, and further containing in the ring 0 to 3 heteroatoms of the same or different types selected from oxygen, nitrogen, or sulfur. It is still more preferable to use quinolyl.

The protecting group for the "hydroxyl protected by a protecting group" is lower alkylsilyl, lower alkyldiphenylsilyl, lower alkyl lower alkoxyphenylsilyl, or lower alkoxydiphenylsilyl.

In this specification, "lower alkyl" refers to $C_{1-6}$ straight or branched alkyl, unless otherwise defined. Specific examples include methyl, ethyl, n-propyl, isopropyl, n-butyl, isobutyl, sec-butyl, tert-butyl, pentyl, hexyl, and the like.

In this specification, "lower alkoxy" refers to alkoxy whose alkyl moiety is a lower alkyl listed above, unless otherwise defined.

Examples of lower alkylsilyl include triethylsilyl, triisopropylsilyl, dimethylisopropylsilyl, tert-butyldimethylsilyl, di-tert-butylmethylsilyl, and the like. Examples of lower alkyldiphenylsilyl include tert-butyldiphenylsilyl and the like. Examples of lower alkyl lower alkoxyphenylsilyl include tert-butylmethoxyphenylsilyl and the like. Examples of lower alkoxydiphenylsilyl include tert-butoxydiphenylsilyl and the like. Of these protecting groups, in particular, tert-butyldimethylsilyl, triisopropylsilyl, tert-butyldiphenylsilyl, and the like are preferable, and tert-butyldimethylsilyl and the like are most preferable.

Alkyloxycarbonyl which may be substituted as used herein as a protecting group for amino or $C_{1-6}$ alkylamino represented by $R_2$ or $R_2'$ is not particularly limited. Examples include alkyloxycarbonyl, whose alkyl moiety has 1 to 6 carbon atoms (e.g., 1 to 4 carbon atoms) and which may be substituted, and the like. Examples of substituents for alkyloxycarbonyl include halogen, adamantyl, trimethylsilyl, phenyl, methoxyphenyl, nitrophenyl, anthryl, fluorenyl, and the like. When substituted, alkyloxycarbonyl is substituted with, for example, one to three substituents. Specific examples of alkyloxycarbonyl which may be substituted include lower alkoxycarbonyl groups, such as methoxycarbonyl, ethoxycarbonyl, tert-butoxycarbonyl; 1-adamantyloxycarbonyl; 2-adamantyloxycarbonyl; 2,2,2-trichloroethoxycarbonyl; 2-trimethylsilylethoxycarbonyl; aralkyloxycarbonyl groups, such as benzyloxycarbonyl, 3,5-di-tert-butylbenzyloxycarbonyl, p-methoxybenzyloxycarbonyl, p-nitrobenzyloxycarbonyl, phenethyloxycarbonyl, and 9-anthrylmethoxycarbonyl; 9-fluorenylmethoxycarbonyl; and the like. In particular, tert-butoxycarbonyl, benzyloxycarbonyl, 9-fluorenylmethoxycarbonyl, and the like are preferable, with tert-butoxycarbonyl being most preferable.

The "$C_{1-6}$ alkylamino" represented by $R_2$ or $R_2'$ of the formulae represents mono($C_{1-6}$ alkyl)amino. Specific examples include methylamino, ethylamino, n-propylamino, isopropylamino, n-butylamino, isobutylamino, and the like, with mono($C_{1-4}$ alkyl)amino being preferable, and methylamino being more preferable.

In this specification, protected $C_{1-6}$ alkylamino refers to an amino group, in which one of the hydrogen atoms of the amino group is replaced by $C_{1-6}$ alkyl, and the other is replaced by alkyloxycarbonyl which may be substituted.

In this specification, protected $C_{1-6}$ alkylamino is preferably protected $C_{1-4}$ alkylamino, and more preferably protected methylamino.

In this specification, the protecting group for thiol protected by a protecting group is aralkyl, benzyloxymethyl, benzylthiomethyl, lower alkoxycarbonyl, 2,2,2-trichloroethoxycarbonyl, 9-fluorenylmethoxycarbonyl, tert-butylsulfanyl, or 3-nitro-2-pyridinesulfenyl. Examples of aralkyl include, but are not particularly limited to, benzyl, p-methoxybenzyl, o-nitrobenzyl, p-nitrobenzyl, diphenylmethyl, triphenylmethyl, and the like. Examples of lower alkoxycarbonyl include, but are not limited to, tert-butoxycarbonyl and the like. Among these protecting groups, in particular, p-methoxybenzyl, tert-butoxycarbonyl, 9-fluorenylmethoxycarbonyl, and the like are preferable, and tert-butoxycarbonyl is most preferable.

In the compound represented by Formulae (1) and (2), $R_1$, $R_2$, and $R_2'$ may be the following:

$R_1$ is hydrogen, $C_{1-6}$ alkyl which may be substituted, $C_{3-10}$ cycloalkyl which may be substituted, $C_{6-14}$ aromatic hydrocarbon which may be substituted, 4- to 10-membered saturated heterocycle which may be substituted, or 4- to 10-membered unsaturated heterocycle which may be substituted; and one of $R_2$ or $R_2'$ is hydroxyl protected by a protecting group selected from the group consisting of lower alkylsilyl, lower alkyldiphenylsilyl, lower alkyl lower alkoxyphenylsilyl, and lower alkoxydiphenylsilyl, amino protected by alkyloxycarbonyl which may be substituted, or thiol protected by a protecting group selected from the group consisting of aralkyl, benzyloxymethyl, benzylthiomethyl, lower alkoxycarbonyl, 2,2,2-trichloroethoxycarbonyl, 9-fluorenylmethoxycarbonyl, tert-butylsulfanyl, and 3-nitro-2-pyridinesulfenyl.

$R_1$, $R_2$, and $R_2'$ may also be the following:

$R_1$ is a functional group other than the "$C_{1-6}$ alkyl which may be substituted, $C_{3-10}$ cycloalkyl which may be substituted, $C_{6-14}$ aromatic hydrocarbon which may be substituted, 4- to 10-membered saturated heterocycle which may be substituted, and 4- to 10-membered unsaturated heterocycle which may be substituted" mentioned above; and one of $R_2$ or $R_2'$ is hydroxyl protected by a protecting group selected from the group consisting of lower alkylsilyl, lower alkyldiphenylsilyl, lower alkyl lower alkoxyphenylsilyl, and lower alkoxydiphenylsilyl, amino or $C_{1-6}$ alkylamino protected by alkyloxycarbonyl which may be substituted, or thiol protected by a protecting group selected from the group consisting of aralkyl, benzyloxymethyl, benzylthiomethyl, lower alkoxycarbonyl, 2,2,2-trichloroethoxycarbonyl, 9-fluorenylmethoxycarbonyl, tert-butylsulfanyl, and 3-nitro-2-pyridinesulfenyl group.

$R_1$, $R_2$, and $R_2'$ may further be the following:

$R_1$ is hydrogen, $C_{1-6}$ alkyl which may be substituted, $C_{3-10}$ cycloalkyl which may be substituted, $C_{6-14}$ aromatic hydrocarbon which may be substituted, 4- to 10-membered saturated heterocycle which may be substituted, or 4- to 10-membered unsaturated heterocycle which may be substituted; and one of $R_2$ or $R_2'$ is $C_{1-6}$ alkylamino protected by alkyloxycarbonyl which may be substituted.

In this specification, $R_3$ is preferably amino.

The following shows a preferable combination of m, n, X, $R_1$, $R_2$, $R_2'$, and $R_3$ in terms of the compound represented by Formulae (1) and (2):

m: an integer of 0 to 2;
n: an integer of 0 or more and such that $0 \leq m+n \leq 3$;
X: bromine or iodine;
$R_1$: hydrogen, $C_{1-6}$ alkyl which may be substituted, $C_{3-10}$ cycloalkyl which may be substituted, $C_{6-14}$ aromatic hydrocarbon which may be substituted, 4- to 10-membered saturated heterocycle which may be substituted, or 4- to 10-membered unsaturated heterocycle which may be substituted;
$R_2$, $R_2'$: one of $R_2$ or $R_2'$ is hydroxyl protected by a protecting group mentioned above, or amino or $C_{1-6}$ alkylamino protected by alkyloxycarbonyl which may be substituted, and the other one of $R_2$ or $R_2'$ is hydrogen; and
$R_3$: amino.

The following shows a more preferable combination of m, n, X, $R_1$, $R_2$, $R_2'$, and $R_3$ in terms of the compound represented by Formulae (1) and (2):

m and n: (m, n)=(0, 1), (1, 1), (0, 2), (2, 1), or (1, 2);
X: bromine or iodine;
$R_1$: hydrogen, $C_{3-7}$ cycloalkyl, $C_{6-14}$ aromatic hydrocarbon, or 4- to 10-membered unsaturated heterocycle;
$R_2$, $R_2'$: one of $R_2$ or $R_2'$ is hydroxyl protected by a protecting group mentioned above, or amino or $C_{1-6}$ alkylamino protected by alkyloxycarbonyl which may be substituted, and the other one of $R_2$ or $R_2'$ is hydrogen; and
$R_3$: amino.

The following shows a still more preferable combination of m, n, X, $R_1$, $R_2$, $R_2'$, and $R_3$ in terms of the compound represented by Formulae (1) and (2):

m and n: (m, n)=(0, 1), (1, 1), (0, 2), (2, 1), or (1, 2);
X: bromine or iodine;
$R_1$: hydrogen, $C_{3-7}$ cycloalkyl, $C_{6-14}$ aromatic hydrocarbon, or monocyclic or bicyclic unsaturated heterocycle containing at least one nitrogen atom in the ring, and further containing in the ring 0 to 3 heteroatoms of the same or different types selected from oxygen, nitrogen, or sulfur;
$R_2$, $R_2'$: one of $R_2$ or $R_2'$ is hydroxyl protected by a protecting group mentioned above, or amino or $C_{1-4}$ alkylamino protected by alkyloxycarbonyl which may be substituted, and the other one of $R_2$ or $R_2'$ is hydrogen; and
$R_3$: amino.

The following shows an even more preferable combination of m, n, X, $R_1$, $R_2$, $R_2'$, and $R_3$ in terms of the compound represented by Formulae (1) and (2):

m and n: (m, n)=(0, 1), (1, 1), or (0, 2);
X: bromine or iodine;
$R_1$: hydrogen, cyclopropyl, phenyl, or quinolyl;
$R_2$, $R_2'$: one of $R_2$ or $R_2'$ is hydroxyl protected by tert-butyldimethylsilyl, or amino or $C_{1-4}$ alkylamino protected by tert-butoxycarbonyl, and the other one of $R_2$ or $R_2'$ is hydrogen; and
$R_3$: amino.

The following shows a still even more preferable combination of m, n, X, $R_1$, $R_2$, $R_2'$, and $R_3$ in terms of the compound represented by Formulae (1) and (2):

m and n: (m, n)=(0, 1), (1, 1), or (0, 2);
X: bromine;
$R_1$: quinolyl;
$R_2$, $R_2'$: $R_2$ is amino or methylamino protected by tert-butoxycarbonyl, and $R_2'$ is hydrogen; and
$R_3$: amino.

The compound represented by Formulae (1) and (2) is preferably represented by Formulae (1) and (2) having the preferable combination of m, n, X, $R_1$, $R_2$, $R_2'$, and $R_3$, and more preferably represented by Formulae (1) and (2) having more preferable combination of m, n, X, $R_1$, $R_2$, $R_2'$, and $R_3$.

The salts of the compounds represented by Formulae (1) and (2) refer to salts commonly used in the field of organic chemistry, and are not limited as long as they do not adversely affect the production method of the present invention. Examples include salts, such as base addition salts of the compound having a carboxyl group with a base added to the carboxyl group; and acid addition salts of the compound having an amino group or a basic heterocyclic group, with an acid added to the amino group or the basic heterocyclic group.

Examples of base addition salts include alkali metal salts, such as sodium salts and potassium salts; alkaline earth metal salts, such as calcium salts and magnesium salts; ammonium salts; and organic amine salts, such as trimethylamine salts, triethylamine salts, dicyclohexylamine salts, ethanolamine salts, diethanolamine salts, triethanolamine salts, procaine salts, and N,N'-dibenzylethylenediamine salts.

Examples of acid addition salts include inorganic acid salts such as hydrochlorides, sulfates, nitrates, phosphates, and perchlorates; organic acid salts such as acetates, formates, maleates, fumarates, tartrates, citrates, ascorbates, and trifluoroacetates; and sulfonates such as methanesulfonates, isethionates, benzenesulfonates, and p-toluenesulfonates.

The following describes a method for producing the compound that is represented by Formula (2) and that is a starting material of the present invention. However, the method for producing the compound that is represented by Formula (2) and that is a starting material of the present invention is not limited to the following.

The compound that is represented by Formula (2) and that is a starting material of the present invention may be produced, for example, by the following production method 1 when $R_1$ represents a functional group, and at least one of $R_2$ or $R_2'$ is amino or $C_{1-6}$ alkylamino protected by alkyloxycarbonyl which may be substituted, or thiol protected by the protecting group mentioned above.

Production Method 1

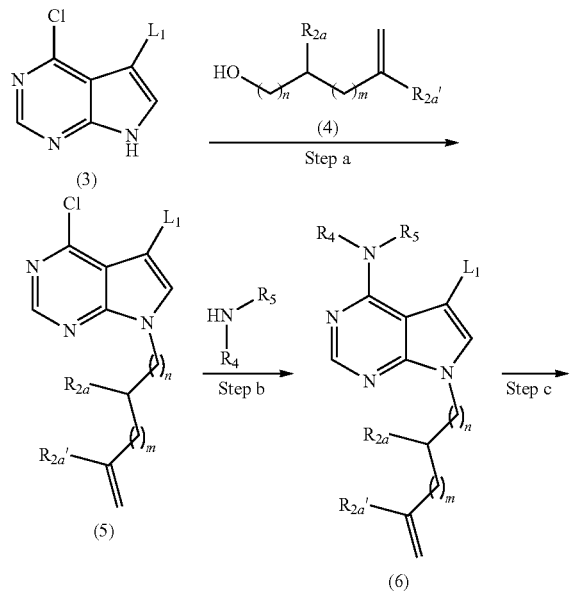

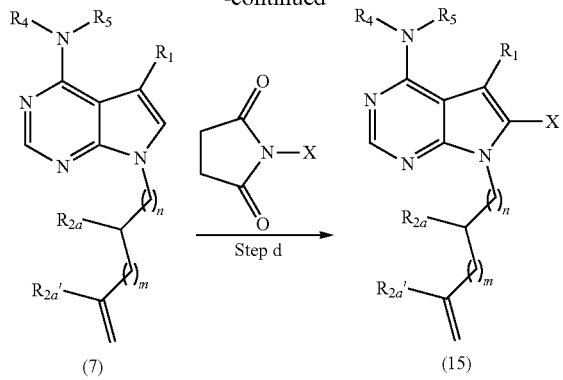

In the formula, $L_1$ represents a leaving group, $R_4$ and $R_5$ represent hydrogen or a substituent for amino, and $R_1$, m, n, and X are as defined above. One of $R_{2a}$ or $R_{2a}'$ is amino or $C_{1-6}$ alkylamino protected by alkyloxycarbonyl which may be substituted, or thiol protected by a protecting group selected from the group consisting of aralkyl, benzyloxymethyl, benzylthiomethyl, lower alkoxycarbonyl, 2,2,2-trichloroethoxycarbonyl, 9-fluorenylmethoxycarbonyl, tert-butylsulfanyl, and 3-nitro-2-pyridinesulfenyl; and the other one of $R_{2a}$ and $R_{2a}'$ is hydrogen.

Step a

In this step, the compound represented by Formula (3) and the compound represented by Formula (4) are used to perform a Mitsunobu reaction to produce the compound represented by Formula (5).

A Mitsunobu reaction may be performed according to a known method (e.g., the method described in Synthesis, p. 1, 1981), or a method similar to this method.

Step b

The "substituent for amino" represented by $R_4$ and $R_5$ refers to the substituents for amino represented by $R_3$ mentioned above. In this step, when $R_4$ and $R_5$ represent hydrogen, i.e., when the amino represented by $R_3$ is not substituted, the compound represented by Formula (5) and ammonia or its salt are subjected to a reaction to produce the compound represented by Formula (6). This step is performed according to a generally known method (e.g., the method described in J. Med. Chem., 2009, 52, 5974-5989). When $R_4$ and $R_5$ do not represent hydrogen, this step can be performed according to a similar method.

Step c

In this step, $R_1$ is introduced to the compound represented by Formula (6) to produce the compound represented by Formula (7).

This step can be performed according to a generally known method (e.g., Chemical Reviews, vol. 95, p. 2457, 1995), in the presence of a transition metal catalyst and a base in a solvent that does not adversely affect the reaction.

A boronic acid or boronic acid ester corresponding to $R_1$ may be synthesized according to a generally known method. When a halogen compound corresponding to $R_1$ is easily obtained, it is possible to convert the compound represented by Formula (6) into a boronic acid or boronic acid ester, and then produce the compound represented by Formula (7) by using a similar method.

Step d

In this step, halogen is introduced into the compound (7) to produce the compound that is represented by Formula (15) and that is a starting material of the present invention.

The halogenation may be performed by the method disclosed in WO 2006/102079, or by a method similar thereto. For example, when bromination is performed, N-bromosuccinimide may be used.

The compound that is represented by Formula (2) and that is a starting material of the present invention may be produced, for example, by the following production method 2 when $R_1$ is a functional group, and at least one of $R_2$ or $R_2$' is hydroxyl protected by a protecting group mentioned above.

Production Method 2

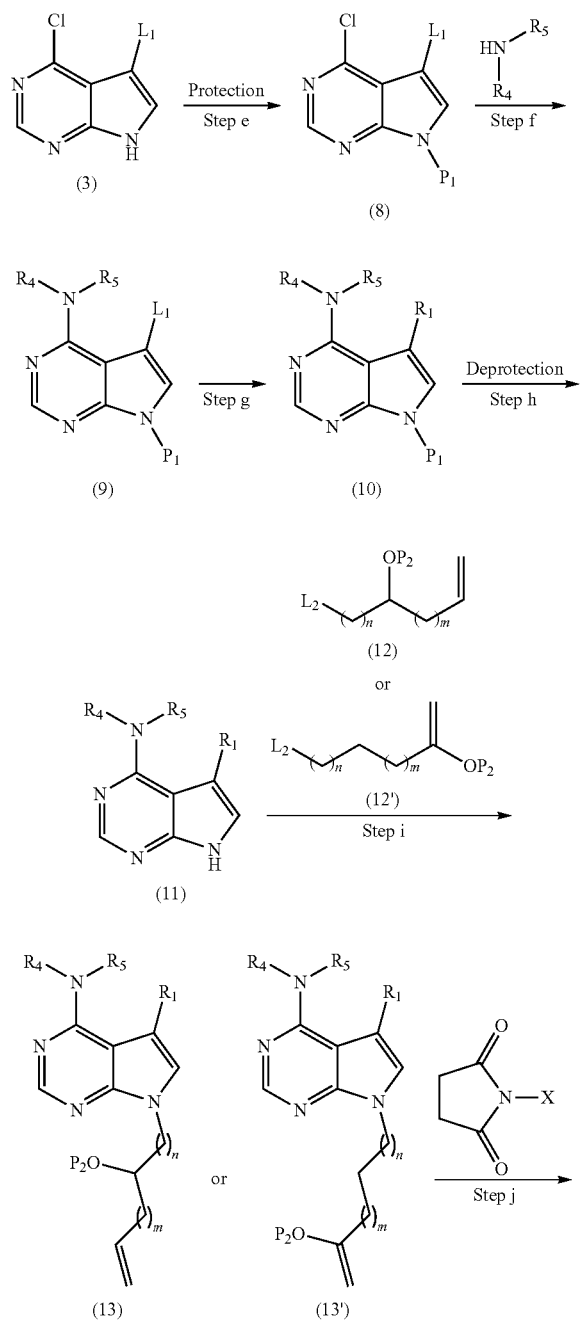

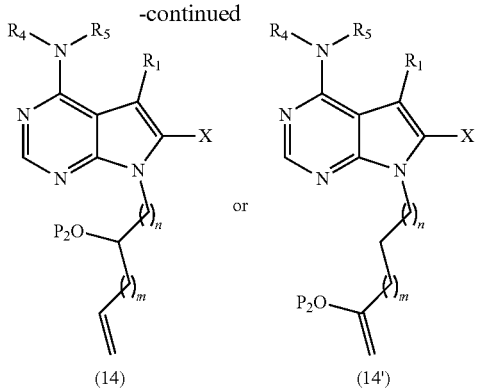

In the formula, $P_1$ represents a protecting group for amino, $P_2$ represents a protecting group for hydroxyl, $L_1$ and $L_2$ are leaving groups, and $R_4$ and $R_5$ are substituents for amino; and $R_1$, m, and X are as defined above.

Step e

In this step, the amino group of the compound represented by Formula (3) is protected to produce the compound represented by Formula (8).

The amino group may be protected by using a generally known method (e.g., the method described in Protective Groups in Organic Synthesis, T.W. Greene, John Wiley & Sons (1981)), or a method similar to this method.

The protecting group for the amino group represented by $P_1$ is not limited as long as it does not adversely affect the above step. Examples include trityl, p-methoxybenzyl, 2-(trimethylsilyl)ethoxymethyl, and the like.

Steps f and g

Step f may be performed as in step b, and step g may be performed as in step c.

Step h

In this step, the protected amino group of the compound represented by Formula (10) is deprotected to produce the compound represented by Formula (11). The deprotection of amino group may be performed by a generally known method (e.g., the method described in Protective Groups in Organic Synthesis, T. W. Greene, John Wiley & Sons (1981)), or a method similar thereto.

Step i

In this step, the compound represented by Formula (11) and the compound represented by Formula (12) or (12') are used to produce the compound represented by Formula (13) or (13') by using a generally known method (e.g., the method described in J. Med. Chem., 2009, 52, 5974-5989) or a method similar to this method, under basic conditions. The protecting group for hydroxyl represented by $P_2$ may be the protecting group mentioned above in relation to "hydroxyl protected by a protecting group" represented by $R_2$ and $R_2$'.

Step j

This step may be performed as in step d.

When $R_1$ of the compound that is represented by Formula (2) and that is a starting material of the present invention is hydrogen, it is possible to produce the compound represented by Formula (14) or (14') as in steps a and b by using, for example, 6-bromo-4-chloro-7H-pyrrolo[2,3-d]pyrimidine or 4-chloro-6-iodo-7H-pyrrolo[2,3-d]pyrimidine, in place of the compound represented by Formula (3).

The method of the present invention for producing a pyrrolopyrimidine ring-containing tricyclic compound represented by Formula (1) comprises the following steps.

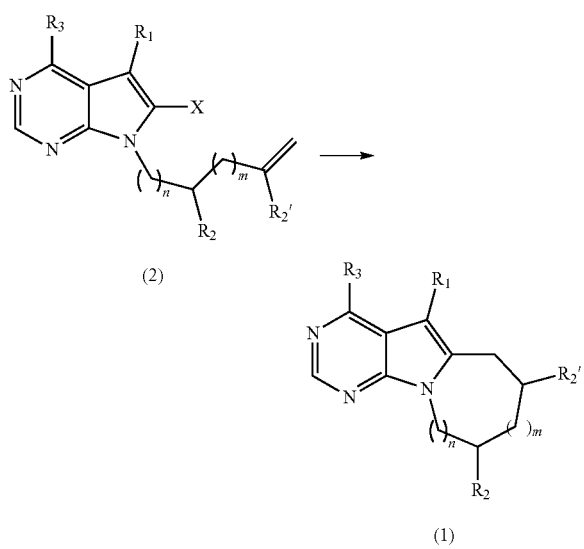

In the formula, $R_1$, $R_2$, $R'_2$, $R_3$, X, m, and n are as defined above. More specifically, the method comprises a step of causing an organic borane reagent to act on a pyrrolopyrimidine derivative represented by Formula (2) or a salt thereof; and a step of performing intramolecular cyclization reaction in the presence of an alkali metal hydroxide using a zerovalent palladium catalyst.

Examples of organic borane reagents include 9-BBN (9-borabicyclo[3.3.1]nonane), 9-BBN (9-borabicyclo[3.3.1]nonane)dimer, disiamylborane(bis(1,2-dimethylpropyl)borane), thexylborane((1,1,2-trimethylpropyl)borane), and the like. The organic borane reagent is preferably 9-BBN (9-borabicyclo[3.3.1]nonane) or 9-BBN (9-borabicyclo[3.3.1]nonane)dimer, and more preferably 9-BBN (9-borabicyclo[3.3.1]nonane). The amount of the organic borane reagent used is not particularly limited insofar as an alkyl borane intermediate is produced. The organic borane reagent may be used in an amount of 1 to 20 moles per mole of the compound represented by Formula (2); the amount of the organic borane reagent is preferably 6 to 10 moles from the viewpoint of facilitating the progress of the reaction.

When the organic borane reagent is caused to act on a pyrrolopyrimidine derivative represented by Formula (2) or a salt thereof, it is believed that an alkyl borane intermediate is produced.

In the production method of the present invention, the production of alkyl borane intermediate in the system may be confirmed after the organic borane reagent is caused to act on a pyrrolopyrimidine derivative represented by Formula (2). For example, LCMS spectra may be used as the confirmation method.

Examples of alkali metal hydroxides include lithium hydroxide, sodium hydroxide, potassium hydroxide, cesium hydroxide, and the like. It is preferable to use lithium hydroxide, sodium hydroxide, potassium hydroxide, or cesium hydroxide. It is more preferable to use lithium hydroxide or sodium hydroxide. The amount of the alkali metal hydroxide used is not particularly limited insofar as the intramolecular cyclization reaction proceeds. The alkali metal hydroxide may be used in an amount of 1 to 100 moles, and preferably 2 to 20 moles, per mole of the compound represented by Formula (2). The alkali metal hydroxide may be used in the form of an aqueous alkali metal hydroxide solution.

Examples of zerovalent palladium catalysts include tetrakis(triphenylphosphine)palladium(0), tris(dibenzylideneacetone)dipalladium(0), palladium carbon(0), and the like. It is preferable to use tetrakis(triphenylphosphine)palladium(0) or tris(dibenzylideneacetone)dipalladium(0), and it is more preferable to use tetrakis(triphenylphosphine)palladium(0). The amount of the zerovalent palladium catalyst used is not particularly limited insofar as the intramolecular cyclization reaction proceeds, and may vary depending on the type of catalyst. The zerovalent palladium catalyst may be used in an amount of 0.0001 to 1 mole, and preferably 0.01 to 0.5 moles, per mole of the compound represented by Formula (2).

In addition to the zerovalent palladium catalyst, a ligand may further be added, if necessary. Examples of ligands include triphenylphosphine, 1,1'-bis(diphenylphosphino)ferrocene, tri-tert-butylphosphine, tricyclohexylphosphine, 2-dicyclohexylphosphino-2',6'-dimethoxybiphenyl, 2-dicyclohexylphosphino-2',4',6'-triisopropylbiphenyl, 2-(di-tert-butylphosphino)biphenyl, 2-dicyclohexylphosphino-2'-(N,N-dimethylamino)biphenyl, 4,5'-bis(diphenylphosphino)-9,9'-dimethylxanthene, and the like. When tris(dibenzylideneacetone)dipalladium(0) is used as a zerovalent palladium catalyst, triphenylphosphine may be added as a ligand. The amount of the ligand used is not particularly limited insofar as the intramolecular cyclization reaction proceeds. The ligand may be used in an amount of 0.0001 to 4 moles, and preferably 0.01 to 2 moles, per mole of the compound of Formula (2).

The combination of an organic borane reagent, an alkali metal hydroxide, and a zerovalent palladium catalyst is preferably a combination of a preferable organic borane reagent, a preferable alkali metal hydroxide, and a preferable zerovalent palladium catalyst, and more preferably a combination of a more preferable organic borane reagent, a more preferable alkali metal hydroxide, and a more preferable zerovalent palladium catalyst. More specifically, it is preferable to use a combination of at least one member selected from the group consisting of 9-BBN (9-borabicyclo[3.3.1]nonane) and 9-BBN (9-borabicyclo[3.3.1]nonane)dimer; at least one member selected from the group consisting of lithium hydroxide, sodium hydroxide, potassium hydroxide, and cesium hydroxide; and at least one member selected from the group consisting of tetrakis(triphenylphosphine)palladium(0) and tris(dibenzylideneacetone)dipalladium(0). It is more preferable to use a combination of 9-BBN (9-borabicyclo[3.3.1]nonane); at least one member selected from the group consisting of lithium hydroxide and sodium hydroxide; and tetrakis(triphenylphosphine)palladium(0).

The combination of the compounds represented by Formulae (1) and (2) with an organic borane reagent, an alkali metal hydroxide, and a zerovalent palladium catalyst is preferably a combination of preferable compounds represented by Formulae (1) and (2) with a preferable organic borane reagent, a preferable alkali metal hydroxide, and a preferable zerovalent palladium catalyst. It is more preferable to use a combination of more preferable compounds represented by Formulae (1) and (2) with a more preferable organic borane reagent, a more preferable alkali metal hydroxide, and a more preferable zerovalent palladium catalyst.

The solvent is not limited insofar as it does not adversely affect the reaction. Examples thereof include hydrocarbons (e.g., benzene, toluene, and xylene), ethers (e.g., 1,2-dimethoxyethane, tetrahydrofuran, and 1,4-dioxane), aprotic polar solvents (e.g., N,N-dimethylformamide, dimethyl sulfoxide, and hexamethyl phosphoryl amide), water, mixtures thereof, and the like. 1,2-Dimethoxyethane or tetrahydrofuran is preferably used. Tetrahydrofuran is particularly preferable from the viewpoint of stability of the organic borane reagent and the generated alkylborane intermediate. The amount of the solvent used is not particularly limited insofar as the reaction proceeds. The solvent may be used in an amount that is 1 to 300 times, and preferably 10 to 96 times, the weight of the compound of Formula (2).

The reaction time is not particularly limited insofar as the compound of Formula (1) is obtained. The reaction time may be 0.1 to 100 hours, and preferably 0.5 to 24 hours.

The reaction temperature is not particularly limited insofar as the compound of Formula (1) is ultimately obtained. The reaction temperature may be −20° C. to the boiling temperature of the solvent, and preferably 0 to 150° C. In the intramolecular cyclization reaction of the alkylborane intermediate using a zerovalent palladium catalyst and an alkali metal hydroxide aqueous solution, a low reaction temperature tends to cause side reactions, which results in a low yield. Therefore, the temperature is preferably 61° C. or higher.

The method of the present invention may further optionally comprise additional steps.

The compound represented by Formula (1) obtained in the present invention may further be isolated and purified. The isolation and purification may be performed by known isolation and purification means, such as concentration, vacuum concentration, crystallization, solvent extraction, reprecipitation, and chromatography.

The compound represented by Formula (1) obtained in the present invention may be subjected to other steps after or without isolation or purification.

When the compound represented by Formula (1) obtained in the present invention has isomers such as optical isomers, stereoisomers, regioisomers, and rotational isomers, any of the isomers and mixtures thereof are included within the scope of the compound, unless otherwise specified. For example, when the compound represented by Formula (1) has optical isomers, the optical isomer separated from a racemic mixture is also included within the scope of the compound of the present invention, unless otherwise specified. Each of such isomers can be obtained as a single compound by known synthesis and separation means (e.g., concentration, solvent extraction, column chromatography, and recrystallization).

As stated above, when the compound represented by Formula (1) has optical isomers, the compound represented by Formula (1) includes each of the enantiomers, as well as a mixture thereof, unless otherwise specified. The compound represented by Formula (1) may be a mixture of R and S enantiomers. Such a mixture may be, for example, a mixture comprising 90% or more, 95% or more, or 99% or more of R enantiomer; or a mixture comprising 90% or more, 95% or more, or 99% or more of S enantiomer.

Methods for chiral resolution include, for example: a diastereomer method, in which a chiral resolving agent is caused to act on the compound represented by Formula (1) to form salts, and a solubility difference etc., of the obtained salts is used to obtain one of the enantiomers; a preferential crystallization method, in which one of the enantiomers is added to a supersaturated solution of a racemic mixture as a seed for crystallization; and a column chromatography method, such as HPLC using a chiral column. A chiral resolving agent usable in the diastereomer method may be appropriately selected from, for example, acid resolving agents such as tartaric acid, malic acid, lactic acid, mandelic acid, 10-camphorsulfonic acid, and derivatives thereof; and basic resolving agents such as brucine, strychnine, quinine, and like alkaloid compounds, amino acid derivatives, cinchonidine, and α-methylbenzylamine. It is possible to obtain one of the enantiomers of the compound represented by Formula (1) not only by obtaining a mixture of enantiomers of the compound represented by Formula (1), followed by the above-described chiral resolution, but also by performing the above-described chiral resolution or the like of the synthetic starting material of the compound represented by Formula (1), and using one of the enantiomers thereof. Methods for obtaining one of the enantiomers of the compound represented by Formula (1) or one of the enantiomers of the starting material compound of the compound represented by Formula (1) include a method of preferentially obtaining one of the enantiomers by adjusting reaction conditions for a catalyst or the like in a reaction step of generating asymmetric carbon.

The compound represented by Formula (1) obtained in the present invention may be subjected to deprotection, introduction of additional side chains, or functional group transformation, and may be used as a production intermediate of medicinal drugs and the like. For example, the compound represented by the following Formula (1'), which is encompassed in Formula (1), and a salt thereof are useful as production intermediates of a quinolylpyrrolopyrimidyl condensed-ring compound, which shows antitumor activity. The present invention also provides a compound represented by the following Formula (1') or a salt thereof.

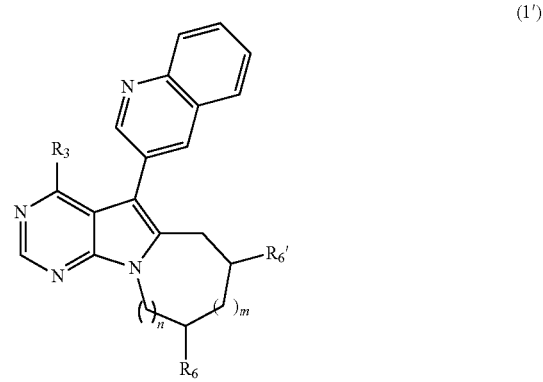

(1')

In the formula, m is an integer of 0 to 2;
n is an integer of 0 or more and such that 0≤m+n≤3;
$R_3$ is amino which may be substituted;
one of $R_6$ or $R_6'$ is amino or $C_{1-6}$ alkylamino protected by alkyloxycarbonyl which may be substituted; and
the other one of $R_6$ or $R_6'$ is hydrogen.

When the compound represented by Formula (1') or its salt is used to perform, for example, the following reaction, a quinolylpyrrolopyrimidyl condensed-ring compound represented by Formula (16), or a salt thereof is obtained.

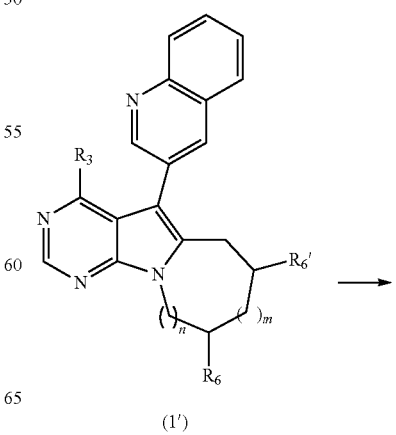

(1')

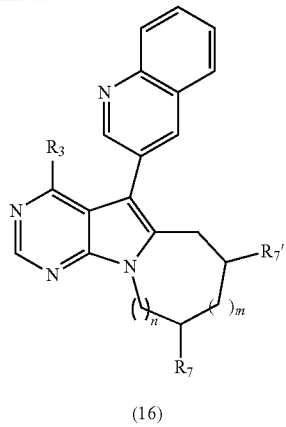

(16)

In the formula, $R_3$, m, and n are as defined above; one of $R_7$ or $R_7'$ is a group represented by the following Formula (17):

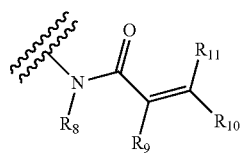

(17)

(wherein $R_8$ is hydrogen or $C_{1-4}$ alkyl;
$R_9$, $R_{10}$, and $R_{11}$ are identical or different and each represent hydrogen, halogen, alkyl, or Formula (a):

$$—CH_2—N(R_{12})(R_{13})$$ (a), (wherein $R_{12}$ and $R_{13}$ are identical or different and each represent hydrogen or $C_{1-4}$ alkyl, or $R_{12}$ and $R_{13}$, taken together with the nitrogen to which they are attached, may form a 4- to 6-membered heterocycloalkyl group)); and the other one of $R_7$ or $R_7'$ is hydrogen.

The method for producing the quinolylpyrrolopyrimidyl condensed-ring compound represented by Formula (16) or a salt thereof from the compound represented by Formula (1') or a salt thereof may comprise the steps of:
A: deprotecting the amino or $C_{1-6}$ alkylamino that is protected by alkyloxycarbonyl which may be substituted and that is represented by one of $R_6$ or $R_6'$ in the compound represented by Formula (1') or a salt thereof; and
B: subjecting the deprotected compound or a salt thereof to amidation.

The deprotection of amino group may be performed by a generally known method, such as the method described in Protective Groups in Organic Synthesis, T.W. Greene, John Wiley & Sons (1981), or a method similar thereto.

When tert-butoxycarbonyl is used as a protecting group, hydrochloric acid, sulfuric acid, methanesulfonic acid, trifluoroacetic acid, or the like may be used as a deprotection reagent. The reagent is preferably used in an amount of 1 to 100 moles per mole of the compound represented by Formula (1').

Any solvents may be used in the reaction insofar as they do not adversely affect the reaction. Examples of usable solvents include water, methanol, ethanol, methylene chloride, chloroform, and the like, and mixtures of these solvents. The reaction time is 0.1 to 100 hours, and preferably 0.5 to 24 hours. The reaction temperature is 0° C. to the boiling point of the solvent.

The thus-obtained deprotected compound may be subjected to the subsequent step B after or without isolation and purification by known isolation and purification means, such as concentration, vacuum concentration, crystallization, solvent extraction, reprecipitation, and chromatography.

In step B (amidation step), the compound obtained in step A is amidated with an α,β-unsaturated carboxylic acid or an α,β-unsaturated acid chloride or bromide to produce the compound of Formula (16) of the present invention.

When a carboxylic acid is used as an amidation reagent, the carboxylic acid is used in an amount of 0.5 to 10 moles, preferably 1 to 3 moles, per mole of the compound obtained in step A, in the presence of a suitable condensation agent. The carboxylic acid may be a commercially available product, or may be produced according to a known method.

The reaction solvent is not limited insofar as it does not adversely affect the reaction. Examples include toluene, benzene, methylene chloride, chloroform, tetrahydrofuran, 1,4-dioxane, N,N-dimethylformamide, dimethylacetamide, N-methylpyrrolidin-2-one, dimethyl sulfoxide, and the like, and mixtures of these solvents. The reaction temperature is generally −78 to 200° C., and preferably 0 to 50° C. The reaction time is generally 5 minutes to 3 days, and preferably 5 minutes to 10 hours.

Examples of condensation agents include diphenylphosphoryl azide, N,N'-dicyclohexylcarbodiimide, benzotriazol-1-yloxy-trisdimethylaminophosphonium salts, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, O-(7-azabenzotriazo-1-yl)-N,N,N',N'-tetramethylhexauronium hexafluorophosphate, and the like.

When an acid chloride or acid bromide is used as an amidation reagent, the acid halide is used in an amount of 0.5 to 5 moles, and preferably 0.9 to 1.1 moles, per mole of the compound obtained in step A. The acid halide may be a commercially available product, or may be produced according to a known method.

The reaction solvent is not limited insofar as it does not adversely affect the reaction. Examples thereof include toluene, benzene, methylene chloride, chloroform, tetrahydrofuran, 1,4-dioxane, N,N-dimethylformamide, dimethylacetamide, N-methylpyrrolidin-2-one, acetonitrile, water, and the like, and mixtures of these solvents. The reaction temperature is typically −78 to 200° C., preferably 0 to 50° C. The reaction time is typically 5 minutes to 3 days, and preferably 5 minutes to 10 hours.

If necessary, a base can be added for the reaction. Examples of usable bases include organic bases, such as triethylamine, diisopropylethylamine, pyridine, lutidine, collidine, 4-(N,N-dimethylamino)pyridine, potassium tert-butyrate, sodium tert-butyrate, sodium methoxide, sodium ethoxide, lithium hexamethyldisilazide, sodium hexamethyldisilazide, potassium hexamethyldisilazide, and butyl lithium; and inorganic bases, such as sodium hydrogen carbonate, sodium carbonate, potassium carbonate, cesium carbonate, sodium hydroxide, and sodium hydride. Such a base may be added in an amount of 1 to 100 moles, preferably 1 to 20 moles, and more preferably 1 to 10 moles per mole of the compound obtained in step A.

The thus-obtained compound of Formula (16) may be isolated and purified by known separation and purification means, such as concentration, vacuum concentration, crystallization, solvent extraction, reprecipitation, and chromatography. The compound represented by Formula (16) or a salt thereof shows antitumor activity as described below.

A preferable mode of $R_3$, m, and n in the compound represented by Formula (1') is as defined above.

Alkyloxycarbonyl which may be substituted as used herein as a protecting group for amino or $C_{1-6}$ alkylamino represented by $R_6$ and $R_6'$ is not particularly limited. Examples include alkyloxycarbonyl, whose alkyl moiety has 1 to 6 carbon atoms (e.g., 1 to 4 carbon atoms) and which may be substituted, and the like. Examples of substituents for alkyloxycarbonyl include halogen, adamantyl, trimethylsilyl, phenyl, methoxyphenyl, nitrophenyl, anthryl, fluorenyl, and the like. When substituted, alkyloxycarbonyl is substituted with, for example, one to three substituents. Specific examples of alkyloxycarbonyl which may be substituted include lower alkoxycarbonyl groups, such as methoxycarbonyl, ethoxycarbonyl, tert-butoxycarbonyl; 1-adamantyloxycarbonyl; 2-adamantyloxycarbonyl; 2,2,2-trichloroethoxycarbonyl; 2-trimethylsilylethoxycarbonyl; aralkyloxycarbonyl groups, such as benzyloxycarbonyl, 3,5-di-tert-butylbenzyloxycarbonyl, p-methoxybenzyloxycarbonyl, p-nitrobenzyloxycarbonyl, phenethyloxycarbonyl, and 9-anthrylmethoxycarbonyl; 9-fluorenylmethoxycarbonyl; and the like. In particular, tert-butoxycarbonyl, benzyloxycarbonyl, 9-fluorenylmethoxycarbonyl, and the like are preferable, with tert-butoxycarbonyl being most preferable.

In this specification, protected $C_{1-6}$ alkylamino refers to an amino group, in which one of the hydrogen atoms of the amino group is replaced by $C_{1-6}$ alkyl, and the other is replaced by alkyloxycarbonyl which may be substituted.

In this specification, protected $C_{1-6}$ alkylamino is preferably protected $C_{1-4}$ alkylamino, and more preferably protected methylamino.

The following shows a preferable combination of m, n, $R_3$, $R_6$, and $R_6'$, in terms of the compound represented by Formula (1'):
m: an integer of 0 to 2;
n: an integer of 0 or more and such that 0≤m+n≤3;
$R_3$: amino;
$R_6$, $R_6'$: one of $R_6$ or $R_6'$ is amino or $C_{1-6}$ alkylamino protected by alkyloxycarbonyl which may be substituted, and the other one of $R_6$ or $R_6'$ is hydrogen.

The following shows a more preferable combination of m, n, $R_3$, $R_6$, and $R_6'$, in terms of the compound represented by Formula (1'):
m and n: (m, n)=(0, 1), (1, 1), (0, 2), (2, 1), or (1, 2);
$R_3$: amino;
$R_6$, $R_6'$: one of $R_6$ or $R_6'$ is amino or $C_{1-6}$ alkylamino protected by alkyloxycarbonyl which may be substituted, and the other one of $R_6$ or $R_6'$ is hydrogen.

The following shows a still more preferable combination of m, n, $R_3$, $R_6$, and $R_6'$, in terms of the compound represented by Formula (1'):
m and n: (m, n)=(0, 1), (1, 1), (0, 2), (2, 1), or (1, 2);
$R_3$: amino;
$R_6$, $R_6'$: one of $R_6$ or $R_6'$ is amino or $C_{1-4}$ alkylamino protected by alkyloxycarbonyl which may be substituted, and the other one of $R_6$ or $R_6'$ is hydrogen.

The following shows an even more preferable combination of m, n, $R_3$, $R_6$, and $R_6'$, in terms of the compound represented by Formula (1'):
m and n: (m, n)=(0, 1), (1, 1), or (0, 2);
$R_3$: amino; and
$R_6$, $R_6'$: one of $R_6$ or $R_6'$ is amino or $C_{1-4}$ alkylamino protected by tert-butoxycarbonyl, and the other one of $R_6$ or $R_6'$ is hydrogen.

The following shows a still even more preferable combination of m, n, $R_3$, $R_6$, and $R_6'$, in terms of the compound represented by Formula (1'):

m and n: (m, n)=(0, 1), (1, 1), or (0, 2);
$R_3$: amino;
$R_6$, $R_6'$: $R_6$ is amino or methylamino protected by tert-butoxycarbonyl, and $R_6'$ is hydrogen.

Examples of preferable compounds of the present invention include the following. However, the compounds of the present invention are not limited to these examples.

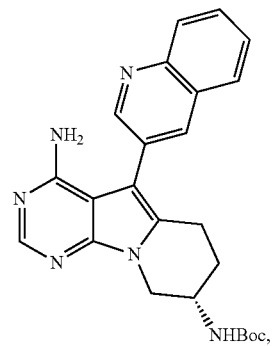

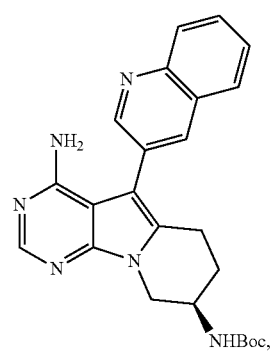

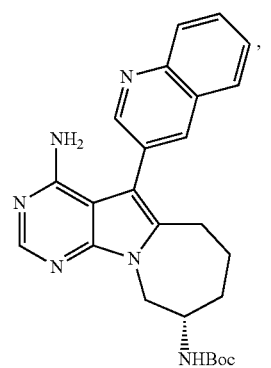

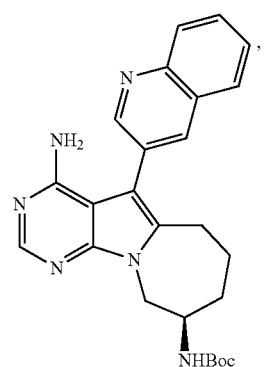

-continued

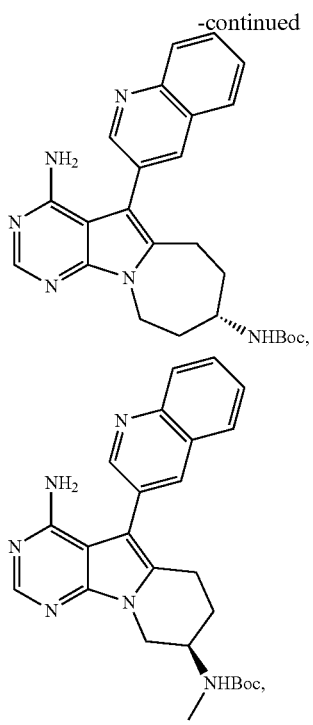

The salts of the compounds represented by Formula (1') refer to salts commonly used in the field of organic chemistry. Examples include salts exemplified above as salts of the compounds represented by Formulae (1) and (2).

The compound represented by Formula (1') or a salt thereof may be produced by the production method of the present invention. However, the method is not limited thereto.

When the compound represented by Formula (1') has isomers such as optical isomers, stereoisomers, regioisomers, and rotational isomers, any of the isomers and mixtures thereof are included within the scope of the compound represented by Formula (1'), unless otherwise specified. For example, when the compound represented by Formula (1') has optical isomers, the optical isomer separated from a racemic mixture is also included within the scope of the compound of the present invention, unless otherwise specified. Each of such isomers can be obtained as a single compound by known synthesis and separation means (e.g., concentration, solvent extraction, column chromatography, recrystallization, etc.).

As stated above, when the compound represented by Formula (1') has optical isomers, the compound represented by Formula (1') includes all of the enantiomers and mixtures thereof, unless otherwise specified. The compound represented by Formula (1') may be a mixture of R and S enantiomers. Such a mixture may be a mixture comprising 90% or more, 95% or more, or 99% or more of R enantiomer; or a mixture comprising 90% or more, 95% or more, or 99% or more of S enantiomer.

Methods for chiral resolution include, for example: a diastereomer method, in which a chiral resolving agent is caused to act on the compound represented by Formula (1') to form salts, and a solubility difference etc., of the obtained salts is used to obtain one of the enantiomers; a preferential crystallization method, in which one of the enantiomers is added to a supersaturated solution of a racemic mixture as a seed for crystallization; and a column chromatography method, such as HPLC using a chiral column. A chiral resolving agent usable in the diastereomer method may be appropriately selected from, for example, acid resolving agents such as tartaric acid, malic acid, lactic acid, mandelic acid, 10-camphorsulfonic acid, and derivatives thereof; and basic resolving agents such as brucine, strychnine, quinine, and like alkaloid compounds, amino acid derivatives, cinchonidine, and α-methylbenzylamine. It is possible to obtain one of the enantiomers of the compound represented by Formula (1') not only by obtaining a mixture of enantiomers of the compound represented by Formula (1'), followed by the above-described chiral resolution, but also by performing the above-described chiral resolution or the like of the synthetic starting material of the compound represented by Formula (1'), and using one of the enantiomers thereof. Methods for obtaining one of the enantiomers of the compound represented by Formula (1') or one of the enantiomers of the starting material compound of the compound represented by Formula (1') include a method of preferentially obtaining one of the enantiomers by adjusting reaction conditions for a catalyst or the like in a reaction step of generating asymmetric carbon.

EXAMPLES

The following Reference Examples, Examples, and Comparative Examples describe the present invention in detail; however, the present invention is not limited to these examples.

The reagents used in the following examples are commercially available reagents unless particularly indicated otherwise. For silica gel column chromatography, the following columns were used: Purif-Pack (registered trademark) SI produced by Moritex Corporation (Shoko Scientific Co., Ltd.), KP-Sil (registered trademark) Silica Prepacked Column produced by Biotage, and HP-Sil (registered trademark) Silica Prepacked Column produced by Biotage. For NMR spectra, AL400 (400 MHz; Nihon Denshi (JEOL Ltd.)), or Mercury 400 (400 MHz; Varian) spectrometer was used. The measurement was carried out using tetramethylsilane as an internal standard when tetramethylsilane was contained in a deuterated solvent; otherwise, an NMR solvent was used as an internal standard. The value δ is indicated in ppm. The microwave reaction was carried out using an initiator produced by Biotage.

LCMS spectra were measured with SQD produced by Waters under the following conditions.
Column: Acquity BEH C18, 1×50 mm, 1.7 μm
MS Detection: ESI positive
UV Detection: 254 and 210 nm
Column Flow Rate: 0.5 mL/min
Mobile Phase: water/acetonitrile (0.1% formic acid)
Amount of Injection: 1 μL

| Gradient (Table 1) | | |
|---|---|---|
| Time (min) | Water | Acetonitrile |
| 0 | 95 | 5 |
| 0.1 | 95 | 5 |
| 2.1 | 5 | 95 |
| 3.0 | STOP | |

The following defines the abbreviations.
s: singlet
d: doublet
t: triplet dd: double doublet
ddd: double double doublet
m: multiplet
br: broad
DMSO-$d_6$: deuterated dimethyl sulfoxide
CDCl$_3$: deuterated chloroform
DME: 1,2-dimethoxyethane
DMF: N,N-dimethylformamide Reference Example 1

Synthesis of (S)-tert-butyl(1-(4-amino-6-bromo-5-(quinolin-3-yl)-7H-pyrrolo[2,3-d]pyrimidin-7-yl)but-3-en-2-yl)carbamate

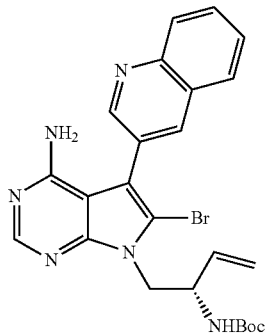 [SMILES: C=C[C@@H](Cn1c(Br)c(-c2cnc3ccccc3c2)c2c(N)ncnc21)NC(=O)OC(C)(C)C]

Step 1

Synthesis of (S)-tert-butyl(1-(4-chloro-5-iodo-7H-pyrrolo[2,3-d]pyrimidin-7-yl)but-3-en-2-yl)carbamate

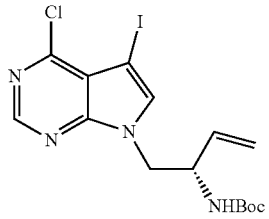 [SMILES: C=C[C@@H](Cn1cc(I)c2c(Cl)ncnc21)NC(=O)OC(C)(C)C]

Diisopropyl azodicarboxylate (2.44 ml) was slowly added to a solution of triphenylphosphine (13.1 g) in tetrahydrofuran (70 ml) with ice-cooling. The reaction mixture was stirred with ice-cooling for one hour, and then a solution of (S)-tert-butyl(1-hydroxybut-3-en-2-yl)carbamate (7.0 g) synthesized in accordance with the procedure disclosed in a non-patent document (Org. Lett., 2005, vol. 7, No. 5, pp. 847-849) and 4-chloro-5-iodo-7H-pyrrolo[2,3-d]pyrimidine (6.97 g) in tetrahydrofuran (35 ml) was slowly added thereto. After the reaction mixture was stirred at room temperature for 2 hours, the solvent was distilled off under reduced pressure. The obtained residue was purified by silica gel column chromatography (developing solvent: hexane/ethyl acetate), thereby giving 20.84 g of the title compound as a pale yellow oily substance. ESI-MS m/z 448, 450 (MH+)

Step 2

Synthesis of (S)-tert-butyl(1-(4-amino-5-iodo-7H-pyrrolo[2,3-d]pyrimidin-7-yl)but-3-en-2-yl)carbamate

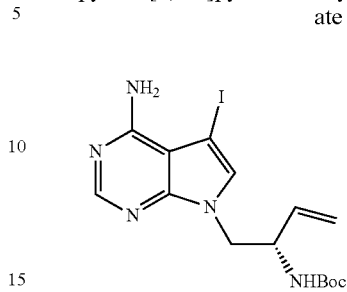

A solution of 8N ammonia in methanol (89.4 ml) was added to the (S)-tert-butyl(1-(4-chloro-5-iodo-7H-pyrrolo[2,3-d]pyrimidin-7-yl)but-3-en-2-yl)carbamate (20.84 g) obtained in Step 1, and the mixture was stirred at 120° C. in an autoclave for 6 hours. After the reaction mixture was cooled with ice, the solvent was distilled off under reduced pressure. The obtained residue was diluted with a small amount of methanol, and the precipitate was filtered, followed by washing with cold methanol (11 ml) and drying under reduced pressure, thereby giving 8.28 g of the title compound as a milky white solid.
ESI-MS m/z 430 (MH+)

Step 3

Synthesis of (S)-tert-butyl(1-(4-amino-5-(quinolin-3-yl)-7H-pyrrolo[2,3-d]pyrimidin-7-yl)but-3-en-2-yl)carbamate

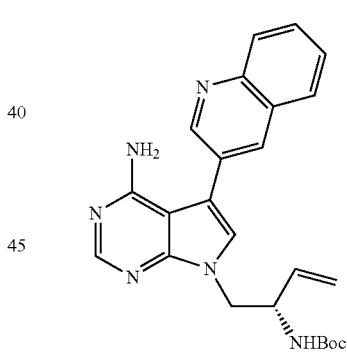

A mixture of the (S)-tert-butyl(1-(4-amino-5-iodo-7H-pyrrolo[2,3-d]pyrimidin-7-yl)but-3-en-2-yl)carbamate obtained in Step 2 (8.26 g), 3-quinolineboronic acid (4.99 g), cesium carbonate (12.54 g), 1,1'-bis(diphenylphosphino)ferrocene palladium(II) dichloride (785.6 mg), DME (66 ml), and water (33 ml) was stirred at 100° C. in a nitrogen atmosphere for 2 hours. After the reaction mixture was cooled, water and ethyl acetate were added thereto, and the organic layer was separated, followed by extraction of the water layer with ethyl acetate twice. The obtained organic layer was dried over anhydrous magnesium sulfate, and the solvent was distilled off under reduced pressure. The obtained residue was purified by silica gel column chromatography (developing solvent: hexane/ethyl acetate, ethyl acetate/methanol), thereby giving 8.0 g of the title compound as a pale orange solid.
ESI-MS m/z 431 (MH+)

Step 4

Synthesis of (S)-tert-butyl(1-(4-amino-6-bromo-5-(quinolin-3-yl)-7H-pyrrolo[2,3-d]pyrimidin-7-yl)but-3-en-2-yl)carbamate

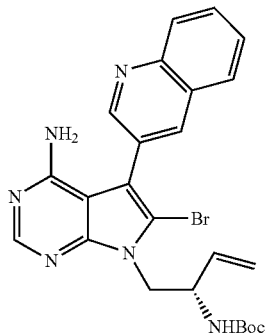 [SMILES: C=C[C@@H](Cn1c(Br)c(-c2cnc3ccccc3c2)c2c(N)ncnc21)NC(=O)OC(C)(C)C]

N-bromosuccinimide (3.63 g) was added to a solution of the (S)-tert-butyl(1-(4-amino-5-(quinolin-3-yl)-7H-pyrrolo[2,3-d]pyrimidin-7-yl)but-3-en-2-yl)carbamate (7.98 g) obtained in Step 3 in DMF (64 ml) at −15° C., and the mixture was stirred at −15° C. for one hour. A 10% aqueous sodium thiosulfate solution and ethyl acetate were added to the reaction mixture, and then the mixture was stirred at room temperature for 10 minutes. The organic layer was separated, and the aqueous layer was extracted with ethyl acetate twice. The obtained organic layer was washed with a saturated sodium chloride solution twice, and dried over anhydrous magnesium sulfate, followed by distillation of the solvent under reduced pressure. The obtained residue was purified by silica gel column chromatography (developing solvent: ethyl acetate/methanol), thereby giving 6.30 g of the title compound as a pale brown solid.

$^1$H-NMR (CDCl$_3$) δ: 1.26 (9H, s), 4.35-4.39 (1H, m), 4.50-4.56 (1H, m), 4.72 (1H, brs), 4.92 (1H, brs), 5.26 (2H, d, J=10.5 Hz) 5.33-5.39 (1H, m), 5.92 (1H, ddd, J=17.2, 10.6, 5.4 Hz), 7.63-7.67(1H, m), 7.79-7.83 (1H, m), 7.90-7.92 (1H, m), 8.19 (1H, d, J=8.3 Hz), 8.27 (1H, d, J=1.7 Hz), 8.35 (1H, s), 9.07 (1H, d, J=2.2 Hz).

ESI-MS m/z 509, 511 (MH+)

Reference Example 2

Synthesis of (R)-tert-butyl(1-(4-amino-6-bromo-5-(quinolin-3-yl)-7H-pyrrolo[2,3-d]pyrimidin-7-yl)but-3-en-2-yl)carbamate

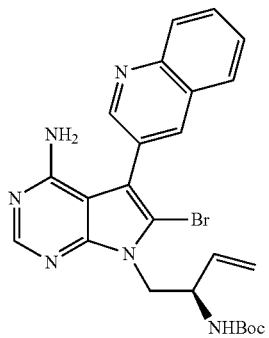 [SMILES: C=C[C@H](Cn1c(Br)c(-c2cnc3ccccc3c2)c2c(N)ncnc21)NC(=O)OC(C)(C)C]

Step 1

Synthesis of (R)-tert-butyl(1-(4-chloro-5-iodo-7H-pyrrolo[2,3-d]pyrimidin-7-yl)but-3-en-2-yl)carbamate

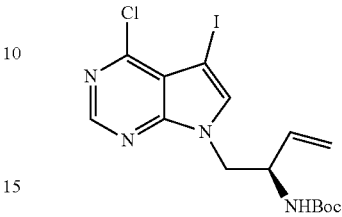

The same procedure as in Step 1 of Reference Example 1 was repeated using (R)-tert-butyl(1-hydroxybut-3-en-2-yl)carbamate (8.74 g) in place of the (S)-tert-butyl(1-hydroxybut-3-en-2-yl)carbamate in Step 1 of Reference Example 1, thereby giving 11.05 g of the title compound as a white solid.

ESI-MS m/z 448, 450 (MH+)

Step 2

Synthesis of (R)-tert-butyl(1-(4-amino-6-bromo-5-(quinolin-3-yl)-7H-pyrrolo[2,3-d]pyrimidin-7-yl)but-3-en-2-yl)carbamate

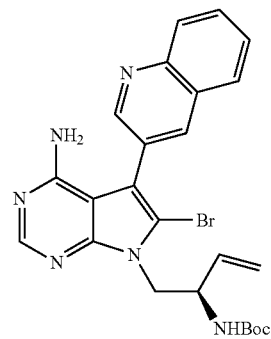 [SMILES: C=C[C@H](Cn1c(Br)c(-c2cnc3ccccc3c2)c2c(N)ncnc21)NC(=O)OC(C)(C)C]

The same procedure as in Steps 2 to 4 of Reference Example 1 was repeated using the (R)-tert-butyl(1-(4-chloro-5-iodo-7H-pyrrolo[2,3-d]pyrimidin-7-yl)but-3-en-2-yl)carbamate (7.88 g) obtained in Step 1 in place of the (S)-tert-butyl(1-(4-chloro-5-iodo-7H-pyrrolo[2,3-d]pyrimidin-7-yl)but-3-en-2-yl)carbamate in Step 2 of Reference Example 1, thereby giving 6.80 g of the title compound as an yellow solid.

$^1$H-NMR (CDCl$_3$) δ: 1.26 (9H, s), 4.35-4.39 (1H, m), 4.50-4.56 (1H, m), 4.72 (1H, brs), 4.92 (1H, brs), 5.26 (2H, d, J=10.5 Hz), 5.33-5.39 (1H, m), 5.92 (1H, ddd, J=17.2, 10.6, 5.4 Hz), 7.63-7.67 (1H, m), 7.79-7.83 (1H, m), 7.90-7.92 (1H, m), 8.19 (1H, d, J=8.3 Hz), 8.27 (1H, d, J=1.7 Hz), 8.35 (1H, s), 9.07 (1H, d, J=2.2 Hz).

ESI-MS m/z 509, 511 (MH+)

Reference Example 3

Synthesis of (S)-tert-butyl(1-(4-amino-6-bromo-7H-pyrrolo[2,3-d]pyrimidin-7-yl)but-3-en-2-yl)carbamate

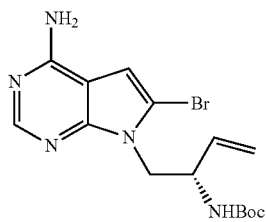 [SMILES: C=C[C@@H](Cn1c(Br)cc2c(N)ncnc21)NC(=O)OC(C)(C)C]

Step 1

Synthesis of (S)-tert-butyl(1-(6-bromo-4-chloro-7H-pyrrolo[2,3-d]pyrimidin-7-yl)but-3-en-2-yl)carbamate

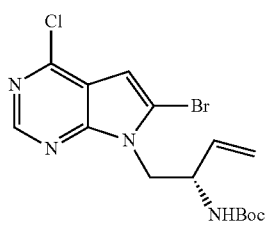 [SMILES: C=C[C@@H](Cn1c(Br)cc2c(Cl)ncnc21)NC(=O)OC(C)(C)C]

The same procedure as in Step 1 of Reference Example 1 was repeated using 2.86 g of 6-bromo-4-chloro-7H-pyrrolo[2,3-d]pyrimidine in place of the 4-chloro-5-iodo-7H-pyrrolo[2,3-d]pyrimidine in Step 1 of Reference Example 1, thereby giving 3.19 g of the title compound as a pale yellow oily substance.

$^1$H-NMR (DMSO-$d_6$) δ: 1.22 (s, 9H), 4.05-4.29 (m, 2H), 4.39-4.54 (m, 1H), 4.92-5.09 (m, 2H), 5.68-5.86 (m, 1H), 6.21 (s, 1H), 7.04 (brs, 1H), 9.50 (s, 1H).

ESI-MS m/z 401 (MH+)

Step 2

Synthesis of (S)-tert-butyl(1-(4-amino-6-bromo-7H-pyrrolo[2,3-d]pyrimidin-7-yl)but-3-en-2-yl)carbamate

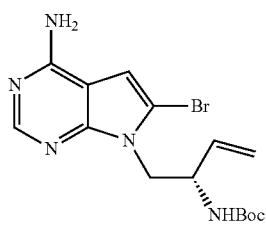 [SMILES: C=C[C@@H](Cn1c(Br)cc2c(N)ncnc21)NC(=O)OC(C)(C)C]

The same procedure as in Step 2 of Reference Example 1 was repeated using 3.19 g of the (S)-tert-butyl(1-(6-bromo-4-chloro-7H-pyrrolo[2,3-d]pyrimidin-7-yl)but-3-en-2-yl)carbamate obtained in Step 1 in place of the (S)-tert-butyl(1-(4-chloro-5-iodo-7H-pyrrolo[2,3-d]pyrimidin-7-yl)but-3-en-2-yl)carbamate in Step 2 of Reference Example 1, thereby giving 3.04 g of the title compound as a white solid.

$^1$H-NMR (DMSO-$d_6$) δ: 1.22 (s, 9H), 4.05-4.29 (m, 2H), 4.39-4.54 (m, 1H), 4.92-5.09 (m, 2H), 5.68-5.86 (m, 1H), 6.69 (s, 1H), 7.04 (brs, 3H), 8.06 (s, 1H).

ESI-MS m/z 382 (MH+)

Reference Example 4

Synthesis of (R)-tert-butyl(1-(4-amino-6-bromo-7H-pyrrolo[2,3-d]pyrimidin-7-yl)but-3-en-2-yl)carbamate

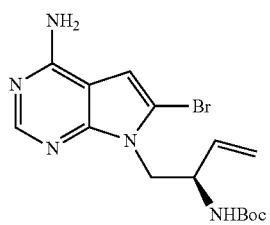 [SMILES: C=C[C@H](Cn1c(Br)cc2c(N)ncnc21)NC(=O)OC(C)(C)C]

Step 1

Synthesis of (R)-tert-butyl(1-(6-bromo-4-chloro-7H-pyrrolo[2,3-d]pyrimidin-7-yl)but-3-en-2-yl)carbamate

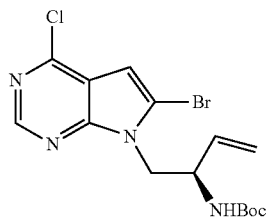 [SMILES: C=C[C@H](Cn1c(Br)cc2c(Cl)ncnc21)NC(=O)OC(C)(C)C]

The same procedure as in Step 1 of Reference Example 1 was repeated using 1.00 g of 6-bromo-4-chloro-7H-pyrrolo[2,3-d]pyrimidine and 1.00 g of (R)-tert-butyl(1-hydroxybut-3-en-2-yl)carbamate in place of the 4-chloro-5-iodo-7H-pyrrolo[2,3-d]pyrimidine and the (S)-tert-butyl(1-hydroxybut-3-en-2-yl)carbamate in Step 1 of Reference Example 1, respectively, thereby giving 1.35 g of the title compound as a pale yellow oily substance.

$^1$H-NMR (DMSO-$d_6$) δ: 1.22 (s, 9H), 4.05-4.29 (m, 2H), 4.39-4.54 (m, 1H), 4.92-5.09 (m, 2H), 5.68-5.86 (m, 1H), 6.21 (s, 1H), 7.04 (brs, 1H) , 9.50 (s, 1H).

ESI-MS m/z 401 (MH+)

Step 2

Synthesis of (R)-tert-butyl(1-(4-amino-6-bromo-7H-pyrrolo[2,3-d]pyrimidin-7-yl)but-3-en-2-yl)carbamate

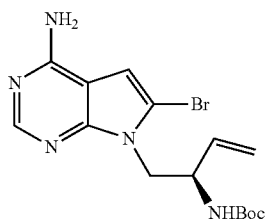 [SMILES: C=C[C@H](Cn1c(Br)cc2c(N)ncnc21)NC(=O)OC(C)(C)C]

The same procedure as in Step 2 of Reference Example 1 was repeated using 1.35 g of the (R)-tert-butyl(1-(6-bromo-4-chloro-7H-pyrrolo[2,3-d]pyrimidin-7-yl)but-3-en-2-yl)carbamate obtained in Step 1 in place of the (S)-tert-butyl (1-(4-chloro-5-iodo-7H-pyrrolo[2,3-d]pyrimidin-7-yl)but-3-en-2-yl)carbamate in Step 2 of Reference Example 1, thereby giving 0.9 g of the title compound as a white solid.
$^1$H-NMR (DMSO-$d_6$) δ: 1.22 (s, 9H), 4.05-4.29 (m, 2H), 4.39-4.54 (m, 1H), 4.92-5.09 (m, 2H), 5.68-5.86 (m, 1H), 6.69 (s, 1H), 7.04 (brs, 3H), 8.06 (s, 1H).
ESI-MS m/z 382 (MH+)

Reference Example 5

Synthesis of (S)-tert-butyl(1-(4-amino-6-iodo-7H-pyrrolo[2,3-d]pyrimidin-7-yl)but-3-en-2-yl)carbamate

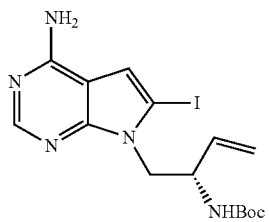 [SMILES: C=C[C@@H](Cn1c(I)cc2c(N)ncnc21)NC(=O)OC(C)(C)C]

Step 1

Synthesis of (S)-tert-butyl(1-(4-chloro-6-iodo-7H-pyrrolo[2,3-d]pyrimidin-7-yl)but-3-en-2-yl)carbamate

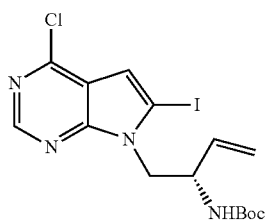 [SMILES: C=C[C@@H](Cn1c(I)cc2c(Cl)ncnc21)NC(=O)OC(C)(C)C]

The same procedure as in Step 1 of Reference Example 1 was repeated using 2.31 g of 4-chloro-6-iodo-7H-pyrrolo[2,3-d]pyrimidine in place of the 4-chloro-5-iodo-7H-pyrrolo[2,3-d]pyrimidine in Step 1 of Reference Example 1, thereby giving 2.61 g of the title compound as an yellow oily substance.
$^1$H-NMR (DMSO-$d_6$) δ: 1.22 (s, 9H), 4.05-4.29 (m, 2H), 4.39-4.54 (m, 1H), 4.92-5.09 (m, 2H), 5.68-5.86 (m, 1H), 6.21 (s, 1H), 7.00 (brs, 1H), 9.50 (s, 1H).
ESI-MS m/z 449 (MH+)

Step 2

Synthesis of (S)-tert-butyl(1-(4-amino-6-iodo-7H-pyrrolo[2,3-d]pyrimidin-7-yl)but-3-en-2-yl)carbamate

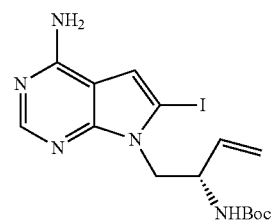

The same procedure as in Step 2 of Reference Example 1 was repeated using 2.61 g of the (S)-tert-butyl(4-chloro-6-chloro-7H-pyrrolo[2,3-d]pyrimidin-7-yl)but-3-en-2-yl)carbamate obtained in Step 1 in place of the (S)-tert-butyl(1-(4-chloro-5-iodo-7H-pyrrolo[2,3-d]pyrimidin-7-yl)but-3-en-2-yl)carbamate in Step 2 of Reference Example 1, thereby giving 2.23 g of the title compound as a white solid.
$^1$H-NMR (DMSO-$d_6$) δ: 1.22 (s, 9H), 4.05-4.29 (m, 2H), 4.39-4.54 (m, 1H), 4.92-5.09 (m, 2H), 5.68-5.86 (m, 1H), 6.50 (s, 1H), 7.00 (brs, 3H), 8.20 (s, 1H).
ESI-MS m/z 430 (MH+)

Reference Example 6

Synthesis of (S)-tert-butyl(1-(4-amino-6-bromo-5-cyclopropyl-7H-pyrrolo[2,3-d]pyrimidin-7-yl)but-3-en-2-yl)carbamate

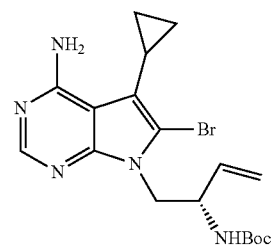 [SMILES: C=C[C@@H](Cn1c(Br)c(C2CC2)c2c(N)ncnc21)NC(=O)OC(C)(C)C]

Step 1

Synthesis of (S)-tert-butyl(1-(4-amino-5-cyclopropyl-7H-pyrrolo[2,3-d]pyrimidin-7-yl)but-3-en-2-yl)carbamate

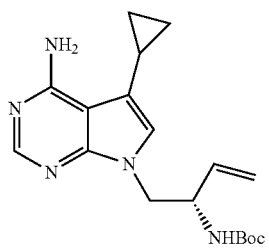

(S)-tert-butyl(1-(4-amino-5-iodo-7H-pyrrolo[2,3-d]pyrimidin-7-yl)but-3-en-2-yl)carbamate (1.000 g), cyclopropylboronic acid (1.787 g), potassium phosphate (2.072 g), tricyclohexylphosphine (84.3 mg), and tetrakis(triphenylphosphine)palladium(0) (136.9 mg) were mixed in toluene (18 ml), and water (1.8 ml) was added thereto. The mixture was degassed under reduced pressure for 1 minute, and nitrogen gas was introduced thereto, followed by heating with stirring at 100° C. for 1.5 hours using a microwave reactor. Cyclopropylboronic acid (0.830 g), tricyclohexylphosphine (29.2 mg), and tetrakis(triphenylphosphine)palladium(0) (49.2 mg) were added to the obtained reaction mixture, and the mixture was further heated with stirring at 100° C. for 1.5 hours. The reaction mixture was poured into a saturated sodium bicarbonate aqueous solution, and extracted with ethyl acetate, followed by drying of the extract over anhydrous sodium sulfate. After removal of the desiccant, the residue obtained by concentrating the filtrate under reduced pressure was purified by silica gel column chromatography (developing solvent: chloroform/methanol), thereby giving 252.8 mg of the title compound as a pale yellow solid.

$^1$H-NMR (CDCl$_3$) δ: 0.62-0.72 (2H, m), 0.86-0.93 (2H, m), 1.33 (9H, s), 1.87-1.96 (1H, m), 4.23 (2H, brs), 4.42-4.52 (1H, m), 5.16 (1H, d, J=10.2 Hz), 5.24 (1H, d, J=17.8 Hz), 5.33-5.50 (2H, br), 5.43 (1H, s), 5.78 (1H, m), 6.66 (1H, s), 8.25 (1H, s).

ESI-MS m/z 344 (MH+)

Step 2

Synthesis of (S)-tert-butyl(1-(4-amino-6-bromo-5-cyclopropyl-7H-pyrrolo[2,3-d]pyrimidin-7-yl)but-3-en-2-yl)carbamate

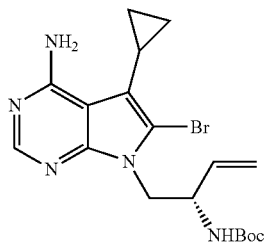

The same procedure as in Step 4 of Reference Example 1 was repeated using 252.8 mg of (S)-tert-butyl(1-(4-amino-5-cyclopropyl-7H-pyrrolo[2,3-d]pyrimidin-7-yl)but-3-en-2-yl)carbamate in place of the (S)-tert-butyl(1-(4-amino-5-(quinolin-3-yl)-7H-pyrrolo[2,3-d]pyrimidin-7-yl)but-3-en-2-yl)carbamate in Step 4 of Reference Example 1, thereby giving 273.2 mg of the title compound as a pale yellow solid.

$^1$H-NMR (CDCl$_3$) δ: 0.75-0.90 (2H, m), 0.98-1.08 (2H, m), 1.23 (9H, s), 1.82 (1H, m), 4.20 (1H, dd, J=14.1, 4.6 Hz), 4.35 (1H, dd, J=14.8-10.5 Hz), 4.50-4.61 (1H, m), 5.20 (1H, d, J=9.7 Hz), 5.30 (1H, d, J=17.3 Hz), 5.40 (1H, d, J=7.8 Hz), 5.57 (1H, brs), 5.84 (1H, m), 8.21 (1H, s).

ESI-MS m/z 422 (MH+)

Reference Example 7

Synthesis of (S)-tert-butyl(1-(4-amino-6-bromo-5-phenyl-7H-pyrrolo[2,3-d]pyrimidin-7-yl)but-3-en-2-yl)carbamate

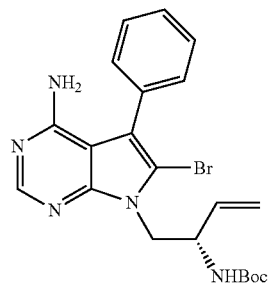 [SMILES: C=C[C@@H](Cn1c(Br)c(-c2ccccc2)c2c(N)ncnc21)NC(=O)OC(C)(C)C]

Step 1

Synthesis of (S)-tert-butyl(1-(4-amino-5-phenyl-7H-pyrrolo[2,3-d]pyrimidin-7-yl)but-3-en-2-yl)carbamate

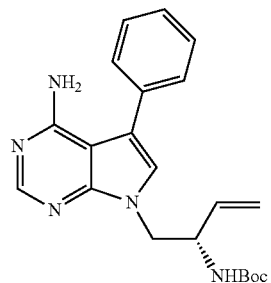 [SMILES: C=C[C@@H](Cn1cc(-c2ccccc2)c2c(N)ncnc21)NC(=O)OC(C)(C)C]

The same procedure as in Step 3 of Reference Example 1 was repeated using 597 mg of phenylboronic acid in place of the 3-quinolineboronic acid in Step 3 of Reference Example 1, thereby giving 1.52 g of the title compound as a white solid.

$^1$H-NMR (CDCl$_3$) δ: 1.33 (9H, s), 4.37 (2H, brs), 4.55-4.61 (1H, m), 5.19-5.21 (3H, m), 5.29 (1H, d, J=16.8 Hz), 5.46 (1H, brs), 5.81-5.89 (1H, m), 6.98 (1H, brs), 7.44-7.49 (5H, m), 8.33 (1H, brs).

ESI-MS m/z 380 (MH+)

Step 2

Synthesis of (S)-tert-butyl(1-(4-amino-6-bromo-5-phenyl-7H-pyrrolo[2,3-d]pyrimidin-7-yl)but-3-en-2-yl)carbamate

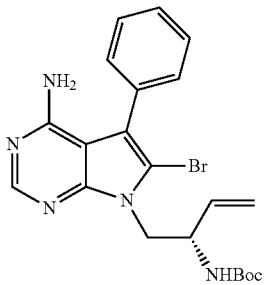 [SMILES: C=C[C@@H](Cn1c(Br)c(-c2ccccc2)c2c(N)ncnc21)NC(=O)OC(C)(C)C]

The same procedure as in Step 4 of Reference Example 1 was repeated using 1.52 g of the (S)-tert-butyl(1-(4-amino-5-phenyl-7H-pyrrolo[2,3-d]pyrimidin-7-yl)but-3-en-2-yl)carbamate obtained in Step 1 in place of the (S)-tert-butyl (1-(4-amino-5-(quinolin-3-yl)-7H-pyrrolo[2,3-d]pyrimidin-7-yl)but-3-en-2-yl)carbamate in Step 4 of Reference Example 1, thereby giving 1.58 g of the title compound as a pale yellow solid.

$^1$H-NMR (CDCl$_3$) δ: 1.25 (9H, s), 4.30-4.34 (1H, m), 4.45-4.51 (1H, m), 4.63-4.73 (1H, m), 5.01 (2H, brs), 5.24 (1H, d, J=10.5 Hz), 5.32-5.37 (1H, m), 5.42-5.44 (1H, m), 5.85-5.94 (1H, m), 7.41-7.50 (5H, m), 8.30 (1H, s).
ESI-MS m/z 458, 460 (MH+)

Reference Example 8

Synthesis of (S)-tert-butyl(1-(4-amino-6-bromo-5-(quinolin-3-yl)-7H-pyrrolo[2,3-d]pyrimidin-7-yl)pent-4-en-2-yl)carbamate

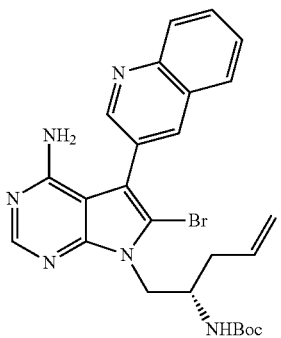 [SMILES: C=CC[C@@H](Cn1c(Br)c(-c2cnc3ccccc3c2)c2c(N)ncnc21)NC(=O)OC(C)(C)C]

Step 1

Synthesis of (S)-tert-butyl(1-(4-chloro-5-iodo-7H-pyrrolo[2,3-d]pyrimidin-7-yl)pent-4-en-2-yl)carbamate

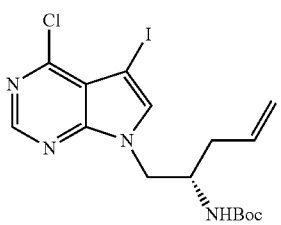 [SMILES: C=CC[C@@H](Cn1cc(I)c2c(Cl)ncnc21)NC(=O)OC(C)(C)C]

The same procedure as in Step 1 of Reference Example 1 was repeated using 11.93 g of (S)-tert-butyl(1-hydroxypent-4-en-2-yl)carbamate in place of the (S)-tert-butyl(1-hydroxybut-3-en-2-yl)carbamate in Step 1 of Reference Example 1, thereby giving 4.96 g of the title compound as a yellowish-brown oily substance.

$^1$H-NMR (CDCl$_3$) δ: 1.35 (9H, s), 2.18-2.35 (2H, m), 3.97-4.05 (1H, m), 4.27-4.33 (1H, m), 4.40-4.45 (1H, m), 4.63-4.65 (1H, m), 5.14-5.19 (2H, m), 5.76-5.86 (1H, m), 7.42 (1H, brs), 8.62 (1H, s).
ESI-MS m/z 462, 464 (MH+)

Step 2

Synthesis of (S)-tert-butyl(1-(4-amino-6-bromo-5-(quinolin-3-yl)-7H-pyrrolo[2,3-d]pyrimidin-7-yl)pent-4-en-2-yl)carbamate

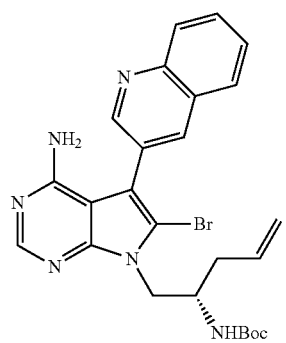 [SMILES: C=CC[C@@H](Cn1c(Br)c(-c2cnc3ccccc3c2)c2c(N)ncnc21)NC(=O)OC(C)(C)C]

The same procedure as in Steps 2 to 4 of Reference Example 1 was repeated using 4.90 g of the (S)-tert-butyl (1-(4-chloro-5-iodo-7H-pyrrolo[2,3-d]pyrimidin-7-yl)pent-4-en-2-yl)carbamate obtained in Step 1 in place of the (S)-tert-butyl (1-(4-chloro-5-iodo-7H-pyrrolo[2,3-d]pyrimidin-7-yl)but-3-en-2-yl)carbamate in Step 2 of Reference Example 1, thereby giving 3.67 g of the title compound as a pale yellow solid.

$^1$H-NMR (CDCl$_3$) δ: 1.23 (9H, s), 2.39-2.42 (2H, m), 4.19-4.27 (1H, m), 4.29-4.34 (1H, m), 4.43-4.50 (1H, m), 4.92 (2H, brs), 5.04 (1H, d, J=8.5 Hz), 5.18-5.24 (2H, m), 5.86-5.96 (1H, m), 7.63-7.67 (1H, m), 7.79-7.83 (1H, m), 7.90-7.92 (1H, m), 8.19 (1H, d, J=8.5 Hz), 8.27 (1H, d, J=1.5 Hz), 8.34 (1H, s), 9.07 (1H, d, J=2.0 Hz).
ESI-MS m/z 523, 525 (MH+)

Reference Example 9

Synthesis of (R)-tert-butyl(1-(4-amino-6-bromo-5-(quinolin-3-yl)-7H-pyrrolo[2,3-d]pyrimidin-7-yl)pent-4-en-2-yl)carbamate

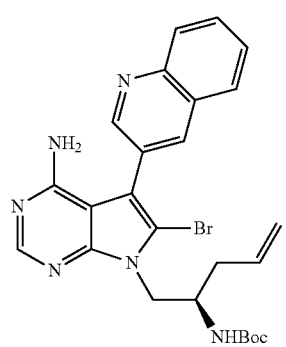 [SMILES: C=CC[C@H](Cn1c(Br)c(-c2cnc3ccccc3c2)c2c(N)ncnc21)NC(=O)OC(C)(C)C]

Step 1

Synthesis of (R)-tert-butyl(1-(4-chloro-5-iodo-7H-pyrrolo[2,3-d]pyrimidin-7-yl)pent-4-en-2-yl)carbamate

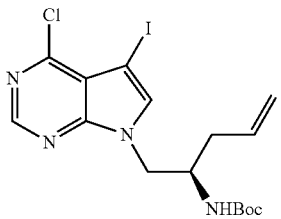 [SMILES: C=CC[C@H](Cn1cc(I)c2c(Cl)ncnc21)NC(=O)OC(C)(C)C]

The same procedure as in Step 1 of Reference Example 1 was repeated using 856.4 mg of (R)-tert-butyl(1-hydroxypent-4-en-2-yl)carbamate in place of the (S)-tert-butyl(1-hydroxybut-3-en-2-yl)carbamate in Step 1 of Reference Example 1, thereby giving 1.54 g of the title compound as a milky white solid.

$^1$H-NMR (CDCl$_3$) δ: 1.35 (9H, s), 2.18-2.35 (2H, m), 3.97-4.05 (1H, m), 4.27-4.33 (1H, m), 4.40-4.45 (1H, m), 4.63-4.65 (1H, m), 5.14-5.19 (2H, m), 5.76-5.86 (1H, m), 7.42 (1H, brs), 8.62 (1H, s).

ESI-MS m/z 462, 464 (MH+)

Step 2

Synthesis of (R)-tert-butyl(1-(4-amino-6-bromo-5-(quinolin-3-yl)-7H-pyrrolo[2,3-d]pyrimidin-7-yl)pent-4-en-2-yl)carbamate

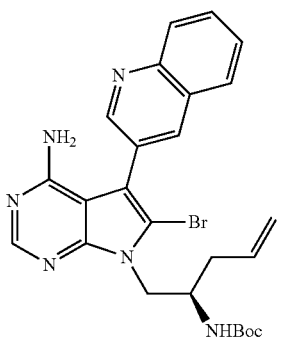 [SMILES: C=CC[C@H](Cn1c(Br)c(-c2cnc3ccccc3c2)c2c(N)ncnc21)NC(=O)OC(C)(C)C]

The same procedure as in Steps 2 to 4 of Reference Example 1 was repeated using 974.9 mg of the (R)-tert-butyl(1-(4-chloro-5-iodo-7H-pyrrolo[2,3-d]pyrimidin-7-yl)pent-4-en-2-yl)carbamate obtained in Step 1 in place of the (S)-tert-butyl(1-(4-chloro-5-iodo-7H-pyrrolo[2,3-d]pyrimidin-7-yl)but-3-en-2-yl)carbamate in Step 2 of Reference Example 1, thereby giving 1.02 g of the title compound as a pale brown solid.

$^1$H-NMR (CDCl$_3$) δ: 1.23 (9H, s), 2.39-2.42 (2H, m), 4.19-4.27 (1H, m), 4.29-4.34 (1H, m), 4.43-4.50 (1H, m), 4.92 (2H, brs), 5.04 (1H, d, J=8.5 Hz), 5.18-5.24 (2H, m), 5.86-5.96 (1H, m), 7.63-7.67 (1H, m), 7.79-7.83 (1H, m), 7.90-7.92 (1H, m), 8.19 (1H, d, J=8.5 Hz), 8.27 (1H, d, J=1.5 Hz), 8.34 (1H, s), 9.07 (1H, d, J=2.0 Hz).

ESI-MS m/z 523, 525 (MH+)

Reference Example 10

Synthesis of (R)-tert-butyl(5-(4-amino-6-bromo-5-(quinolin-3-yl)-7H-pyrrolo[2,3-d]pyrimidin-7-yl)pent-1-en-3-yl)carbamate

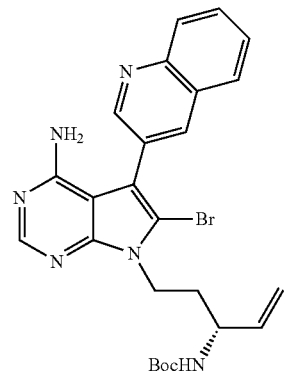 [SMILES: C=C[C@@H](CCn1c(Br)c(-c2cnc3ccccc3c2)c2c(N)ncnc21)NC(=O)OC(C)(C)C]

Step 1

Synthesis of (R)-tert-butyl(5-(4-chloro-5-iodo-7H-pyrrolo[2,3-d]pyrimidin-7-yl)pent-1-en-3-yl)carbamate

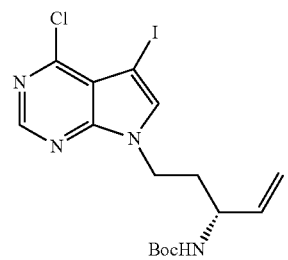 [SMILES: C=C[C@@H](CCn1cc(I)c2c(Cl)ncnc21)NC(=O)OC(C)(C)C]

The same procedure as in Step 1 of Reference Example 1 was repeated using 2.5 g of (R)-tert-butyl(5-hydroxypent-1-en-3-yl)carbamate in place of the (S)-tert-butyl(1-hydroxybut-3-en-2-yl)carbamate in Step 1 of Reference Example 1, thereby giving 3.49 g of the title compound as a pale yellow solid.

ESI-MS m/z 463, 465 (MH+)

Step 2

Synthesis of (R)-tert-butyl(5-(4-amino-6-bromo-5-(quinolin-3-yl)-7H-pyrrolo[2,3-d]pyrimidin-7-yl)pent-1-en-3-yl)carbamate

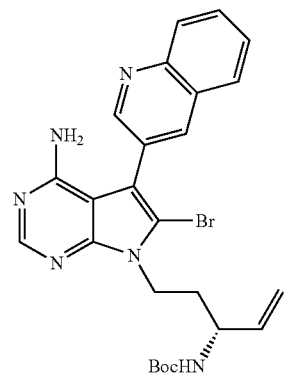 [SMILES: C=C[C@@H](CCn1c(Br)c(-c2cnc3ccccc3c2)c2c(N)ncnc21)NC(=O)OC(C)(C)C]

The same procedure as in Steps 2 to 4 of Reference Example 1 was repeated using 3.21 g of the (R)-tert-butyl (5-(4-chloro-5-iodo-7H-pyrrolo[2,3-d]pyrimidin-7-yl)pent-1-en-3-yl)carbamate obtained in Step 1 in place of the (S)-tert-butyl(1-(4-chloro-5-iodo-7H-pyrrolo[2,3-d] pyrimidin-7-yl)but-3-en-2-yl)carbamate in Step 2 of Reference Example 1, thereby giving 3.15 g of the title compound as a pale brown solid.

$^1$H-NMR (CDCl$_3$) δ: 1.46 (9H, s), 2.02-2.21 (2H, m), 4.26-4.53 (3H, m), 4.90 (2H, brs), 5.07 (1H, d, J=12.4 Hz), 5.15 (1H, d, J=17.2 Hz) 5.15-5.23 (1H, m), 5.78 (1H, ddd, J=17.2, 12.4, 5.2 Hz), 7.61-7.67 (1H, m), 7.78-7.83 (1H, m), 7.88-7.93 (1H, m), 8.17-8.21 (1H, m), 8.26 (1H, d, J=2.2 Hz), 8.35 (1H, s), 9.06 (1H, d, J=2.2 Hz).

ESI-MS m/z 523, 525 (MH+)

Reference Example 11

Synthesis of (R)-6-bromo-7-(2-((tert-butyldimethylsilyl)oxy)but-3-en-1-yl)-5-(quinolin-3-yl)-7H-pyrrolo[2,3-d]pyrimidin-4-amine

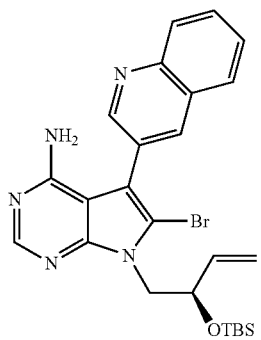 [SMILES: C=C[C@H](Cn1c(Br)c(-c2cnc3ccccc3c2)c2c(N)ncnc21)O[Si](C)(C)C(C)(C)C]

Step 1

Synthesis of 4-chloro-5-iodo-7-((2-(trimethylsilyl)ethoxy)methyl)-7H-pyrrolo[2,3-d]pyrimidine

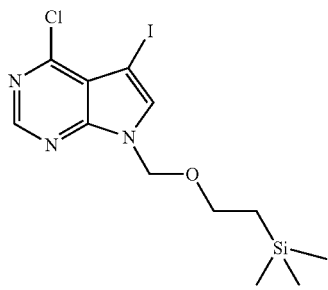 [SMILES: C[Si](C)(C)CCOCn1cc(I)c2c(Cl)ncnc21]

A solution of 4-chloro-5-iodo-7H-pyrrolo[2,3-d]pyrimidine (20.0 g) in DMF (50 ml) was slowly added to a solution of sodium hydride (dispersed in liquid paraffin) (3.4 g) in DMF (190 ml) with ice-cooling, and 2-(trimethylsilyl) ethoxymethyl chloride (13.3 ml) was added thereto, followed by stirring at the same temperature for 2 hours. 2-(trimethylsilyl)ethoxymethyl chloride (1.3 ml) was further added to the reaction mixture, and the mixture was stirred at room temperature for 1 hour. The reaction mixture was added to water (600 ml), and stirred at room temperature for 15 minutes. The obtained precipitate was filtered off, washed with water and diisopropyl ether, and dissolved in ethyl acetate again, followed by filtration to separate off the insoluble substances. The solvent of the filtrate was distilled off under reduced pressure, and heptane was added to the resulting residue to collect a precipitate by filtration, followed by washing with heptane and drying under reduced pressure, thereby giving 21.2 g of the title compound as a white solid.

ESI-MS m/z 409, 411 (MH+)

Step 2

Synthesis of 5-iodo-7-((2-(trimethylsilyl)ethoxy)methyl)-7H-pyrrolo[2,3-d]pyrimidin-4-amine

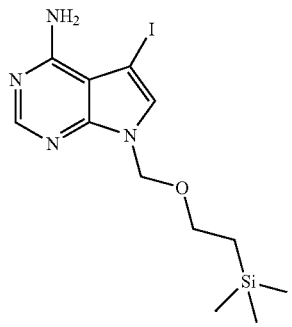 [SMILES: C[Si](C)(C)CCOCn1cc(I)c2c(N)ncnc21]

An 8N ammonia/methanol solution (120 ml) was added to the 4-chloro-5-iodo-7-((2-(trimethylsilyl)ethoxy)methyl)-7H-pyrrolo[2,3-d]pyrimidine (20.0 g) obtained in Step 1, and the mixture was stirred at 120° C. for 1 hour using a microwave reactor. The reaction mixture was cooled, and then diluted with methanol (65 ml) and water (185 ml). The obtained precipitate was filtered off, washed with water, and dried under reduced pressure, thereby giving 15.2 g of the title compound as a white solid.

ESI-MS m/z 391 (MH+)

Step 3

Synthesis of 5-(quinolin-3-yl)-7-((2-(trimethylsilyl)ethoxy)methyl)-7H-pyrrolo[2,3-d]pyrimidin-4-amine

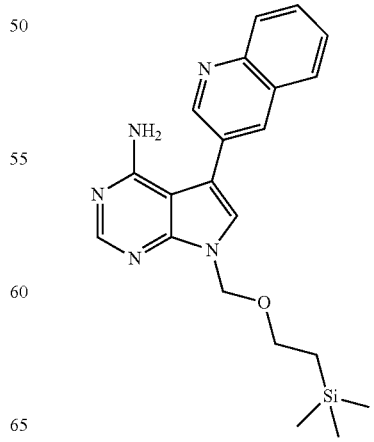

A 2M aqueous sodium carbonate solution (38 ml) was added to a solution of the 5-iodo-7-((2-(trimethylsilyl)ethoxy)methyl)-7H-pyrrolo[2,3-d]pyrimidin-4-amine (15.0 g) obtained in Step 2, 3-quinolineboronic acid (8.6 g), and tetrakis(triphenylphosphine)palladium(0) (2.2 g) in DME (270 ml), and the mixture was stirred at 90° C. in a nitrogen atmosphere for 6 hours. The reaction mixture was cooled, and then water (300 ml) was added thereto, followed by filtration of the obtained precipitate. The filtered precipitate was washed with water and diisopropyl ether, and dried under reduced pressure. The obtained residue was purified by silica gel column chromatography (developing solvent: methanol/chloroform), thereby giving 10.17 g of the title compound as a pale yellow solid.

ESI-MS m/z 392 (MH+)

Step 4

Synthesis of 5-(quinolin-3-yl)-7H-pyrrolo[2,3-d]pyrimidin-4-amine dihydrochloride salt

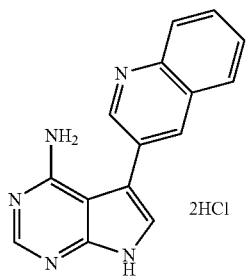 [SMILES: Nc1ncnc2[nH]cc(-c3cnc4ccccc4c3)c12]

Concentrated hydrochloric acid (20 ml) was added at 90° C. to a solution of the 5-(quinolin-3-yl)-7-((2-(trimethylsilyl)ethoxy)methyl)-7H-pyrrolo[2,3-d]pyrimidin-4-amine (10.0 g) obtained in Step 3 in ethanol (200 ml), and the mixture was stirred at the same temperature for 25 minutes. Concentrated hydrochloric acid (30 ml) was added to the mixture, and the mixture was stirred at the same temperature for 75 minutes. The reaction mixture was cooled, and then ethanol (100 ml) was added thereto, followed by stirring at 95° C. for 90 minutes. Subsequently, ethanol (100 ml) and concentrated hydrochloric acid (25 ml) were added thereto, followed by stirring at the same temperature for 4 days. After the reaction mixture was cooled, ethyl acetate was added thereto, and the obtained precipitate was filtered off, followed by washing with ethyl acetate and drying under reduced pressure, thereby giving 4.4 g of the title compound as a yellow solid.

ESI-MS m/z 335 (MH+)

Step 5

Synthesis of (R)-7-(2-((tert-butyldimethylsilyl)oxy)but-3-en-1-yl)-5-(quinolin-3-yl)-7H-pyrrolo[2,3-d]pyrimidin-4-amine

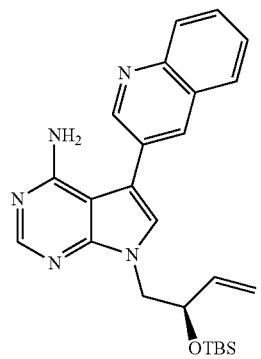 [SMILES: C=C[C@H](Cn1cc(-c2cnc3ccccc3c2)c2c(N)ncnc21)O[Si](C)(C)C(C)(C)C]

Potassium carbonate (4.0 g) and (R)-2-((tert-butyldimethylsilyl)oxy)but-3-en-1-yl 4-methylbenzenesulfonate (1.43 g) were added at room temperature to a solution of the 5-(quinolin-3-yl)-7H-pyrrolo[2,3-d]pyrimidin-4-amine dihydrochloride salt (1.22 g) obtained in Step 4 in DMF (12.2 ml), and the mixture was stirred at 90° C. for 20 hours. After the reaction mixture was cooled, water (49 ml) was added thereto, followed by stirring at room temperature for 3 hours. The obtained precipitate was filtered off, washed with water, and dried under reduced pressure, followed by purification of the obtained residue by silica gel column chromatography (developing solvent: methanol/ethyl acetate), thereby giving 1.31 g of the title compound as a pale yellow solid.

$^1$H-NMR (CDCl$_3$) δ: −0.32 (3H, s), −0.11 (3H, s), 0.80 (9H, s), 4.06 (1H, dd, J=13.9, 8.5 Hz), 4.46 (1H, dd, J=13.9, 3.2 Hz), 4.59-4.64 (1H, m), 5.06 (2H, brs), 5.22 (1H, d, J=10.5 Hz), 5.40 (1H, d, J=16.8 Hz), 5.89-5.97 (1H, m), 7.21 (1H, s), 7.61-7.65 (1H, m), 7.74-7.78 (1H, m), 7.89 (1H, d, J=8.1 Hz), 8.17 (1H, d, J=8.3 Hz), 8.23 (1H, d, J=2.2 Hz), 8.40 (1H, s), 9.10 (1H, d, J=2.0 Hz).

ESI-MS m/z 446 (MH+)

Step 6

Synthesis of (R)-6-bromo-7-(2-((tert-butyldimethylsilyl)oxy)but-3-en-1-yl)-5-(quinolin-3-yl)-7H-pyrrolo[2,3-d]pyrimidin-4-amine

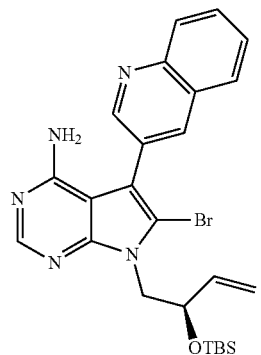 [SMILES: C=C[C@H](Cn1c(Br)c(-c2cnc3ccccc3c2)c2c(N)ncnc21)O[Si](C)(C)C(C)(C)C]

The same procedure as in Step 4 of Reference Example 1 was repeated using 1.30 g of the (R)-7-(2-((tert-butyldimethylsilyl)oxy)but-3-en-1-yl)-5-(quinolin-3-yl)-7H-pyrrolo[2,3-d]pyrimidin-4-amine obtained in Step 5 in place of the (S)-tert-butyl(1-(4-amino-5-(quinolin-3-yl)-7H-pyrrolo[2,3-d]pyrimidin-7-yl)but-3-en-2-yl)carbamate in Step 4 of Reference Example 1, thereby giving 1.44 g of the title compound as a yellow solid.

¹H-NMR (CDCl₃) δ: −0.34 (3H, s), −0.12 (3H, s), 0.75 (9H, s), 4.33-4.40 (2H, m), 4.74-4.79 (1H, m), 4.91 (2H, brs), 5.21-5.24 (1H, m), 5.36-5.41 (1H, m), 5.92-6.01 (1H, m), 7.63-7.67 (1H, m), 7.79-7.83 (1H, m), 7.92 (1H, d, J=7.8 Hz), 8.20 (1H, d, J=8.5 Hz), 8.24 (1H, d, J=2.2 Hz), 8.37 (1H, s), 9.06 (1H, d, J=2.2 Hz).

ESI-MS m/z 524,526 (MH+)

Reference Example 12

Synthesis of (R)-tert-butyl(1-(4-amino-6-bromo-5-(quinolin-3-yl)-7H-pyrrolo[2,3-d]pyrimidin-7-yl)but-3-en-2-yl)(methyl)carbamate

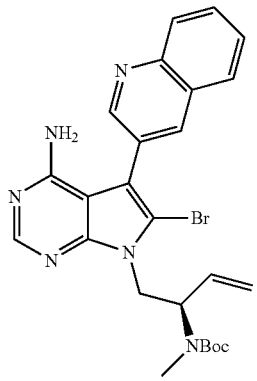 [SMILES: C=C[C@H](Cn1c(Br)c(-c2cnc3ccccc3c2)c2c(N)ncnc21)N(C)C(=O)OC(C)(C)C]

Step 1

Synthesis of (R)-tert-butyl(1-(4-chloro-5-iodo-7H-pyrrolo[2,3-d]pyrimidin-7-yl)but-3-en-2-yl)(methyl)carbamate

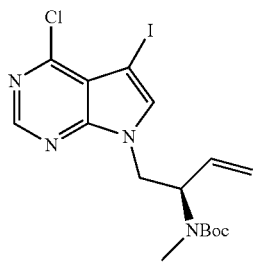 [SMILES: C=C[C@H](Cn1cc(I)c2c(Cl)ncnc21)N(C)C(=O)OC(C)(C)C]

Methyl iodide (1.58 ml) and sodium hydride (224 mg) dispersed in liquid paraffin were added at room temperature to a solution of the (R)-tert-butyl(1-(4-chloro-5-iodo-7H-pyrrolo[2,3-d]pyrimidin-7-yl)but-3-en-2-yl)carbamate (2.28 g) obtained in Step 1 of Reference Example 2 in DMF (11.4 ml). The mixture was stirred at the same temperature for 1 hour, and water was added thereto, followed by extraction with ethyl acetate. The obtained organic layer was washed with water and a saturated sodium chloride solution, and dried over anhydrous sodium sulfate, followed by distillation of the solvent under reduced pressure. The obtained residue was purified by silica gel column chromatography (developing solvent: hexane/ethyl acetate), thereby giving 2.41 g of the title compound as a pale yellow solid.

ESI-MS m/z 463, 465 (MH+)

Step 2

Synthesis of (R)-tert-butyl(1-(4-amino-6-bromo-5-(quinolin-3-yl)-7H-pyrrolo[2,3-d]pyrimidin-7-yl)but-3-en-2-yl)(methyl)carbamate

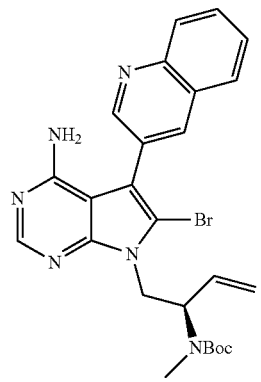 [SMILES: C=C[C@H](Cn1c(Br)c(-c2cnc3ccccc3c2)c2c(N)ncnc21)N(C)C(=O)OC(C)(C)C]

The same procedure as in Steps 2 to 4 of Reference Example 1 was repeated using 2.41 g of the (R)-tert-butyl(1-(4-chloro-5-iodo-7H-pyrrolo[2,3-d]pyrimidin-7-yl)but-3-en-2-yl)(methyl)carbamate obtained in Step 1 in place of the (S)-tert-butyl(1-(4-chloro-5-iodo-7H-pyrrolo[2,3-d]pyrimidin-7-yl)but-3-en-2-yl)carbamate in Step 2 of Reference Example 1, thereby giving 1.61 g of the title compound as a pale brown solid.

¹H-NMR (CDCl₃) δ: 1.21 (9H, s), 2.80-2.95 (3H, m), 4.32-4.50 (1H, m), 4.54-4.79 (1H, m), 4.80-4.92 (2H, m), 5.18-5.42 (3H, m), 5.88-6.02 (1H, m), 7.65 (1H, t, J=8.0 Hz), 7.81 (1H, t, J=8.0 Hz), 7.91 (1H, d, J=8.4 Hz), 8.20 (1H, d, J=8.4 Hz), 8.27 (1H, brs), 8.35 (1H, s), 9.08 (1H, d, J=2.2 Hz).

ESI-MS m/z 523, 525 (MH+)

Reference Example 13

Synthesis of (S)—N-(4-amino-5-(quinolin-3-yl)-7,8,9,10-tetrahydro-6H-pyrimido[5',4':4,5]pyrrolo[1,2-a]azepin-8-yl)acrylamide

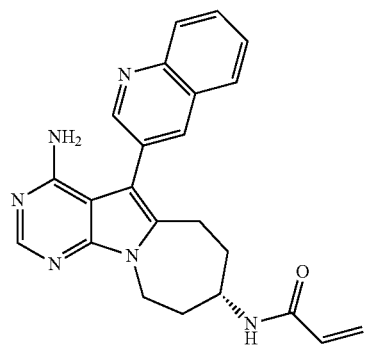 [SMILES: C=CC(=O)N[C@H]1CCc2c(-c3cnc4ccccc4c3)c3c(N)ncnc3n2CC1]

Step 1

Synthesis of (S)-5-(quinolin-3-yl)-7,8,9,10-tetrahydro-6H-pyrimido[5',4':4,5]pyrrolo[1,2-a]azepin-4,8-diamine

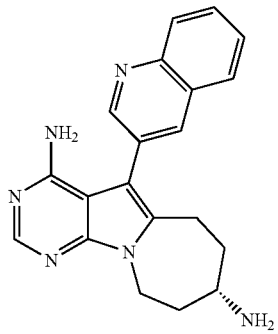 [SMILES: Nc1ncnc2c1c(-c1cnc3ccccc3c1)c1n2CC[C@@H](N)CC1]

5N hydrochloric acid (1 ml) was added at room temperature to a solution of (S)-tert-butyl(4-amino-5-(quinolin-3-yl)-7,8,9,10-tetrahydro-6H-pyrimido[5',4':4,5]pyrrolo[1,2-a]azepin-8-yl)carbamate (436 mg) obtained in the below-described Example 16 in ethanol (4 ml), and the mixture was stirred at 60° C. for 3 hours. The reaction mixture was cooled, and then basified with a 5N aqueous sodium hydroxide solution, followed by extraction with chloroform. The organic layer was dried over anhydrous sodium sulfate, and the solvent was distilled off under reduced pressure. The obtained residue was purified by silica gel column chromatography (developing solvent: chloroform/methanol), thereby giving 320 mg of the title compound as a pale yellow solid.

ESI-MS m/z 345 (MH+)

Step 2

Synthesis of (S)—N-(4-amino-5-(quinolin-3-yl)-7,8,9,10-tetrahydro-6H-pyrimido[5',4':4,5]pyrrolo[1,2-a]azepin-8-yl)acrylamide

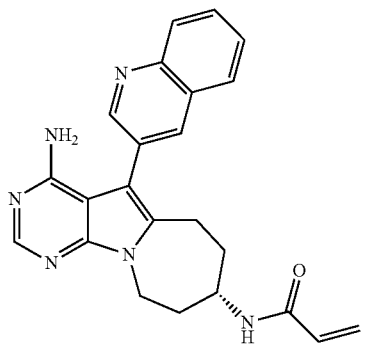 [SMILES: C=CC(=O)N[C@H]1CCc2c(-c3cnc4ccccc4c3)c3c(N)ncnc3n2CC1]

A solution of N,N-diisopropylethylamine (0.192 ml) and acryloyl chloride (83.3 mg) in acetonitrile (0.83 ml) was added to a solution of the (S)-5-(quinolin-3-yl)-7,8,9,10-tetrahydro-6H-pyrimido[5',4':4,5]pyrrolo[1,2-a]azepin-4,8-diamine (317 mg) obtained in Step 1 in acetonitrile (1.6 ml) and water (1.6 ml) with ice-cooling. The mixture was stirred at the same temperature for 15 minutes, and a saturated sodium bicarbonate aqueous solution was poured thereinto, followed by extraction with chloroform. After the organic layer was dried over anhydrous sodium sulfate, the solvent was distilled off under reduced pressure. The obtained residue was purified by silica gel column chromatography (developing solvent: ethyl acetate/methanol), thereby giving 226 mg of the title compound as a pale yellow solid.

$^1$H-NMR (DMSO-$d_6$) δ: 1.37-1.56 (2H, m), 1.98-2.20 (2H, m), 2.75-2.83 (1H, m), 2.88-2.97 (1H, m), 3.96-4.18 (2H, m), 4.78-4.90 (1H, m), 5.58 (1H, dd, J=10.0, 2.2 Hz), 5.93 (2H, brs), 6.19 (1H, dd, J=17.1, 2.2 Hz), 6.21 (1H, dd, J=17.1-10.0 Hz), 7.64 (1H, t, J=7.4 Hz), 7.77 (1H, t, J=7.4 Hz), 8.01-8.09 (2H, m), 8.14 (1H, s), 8.17 (1H, d, J=7.6 Hz), 8.27 (1H, d, J=2.0 Hz), 8.85 (1H, d, J=2.0 Hz).

ESI-MS m/z 399 (MH+)

Reference Example 14

Synthesis of (S)—N-(4-amino-5-(quinolin-3-yl)-7,8,9,10-tetrahydro-6H-pyrimido[5',4':4,5]pyrrolo[1,2-a]azepin-9-yl)acrylamide

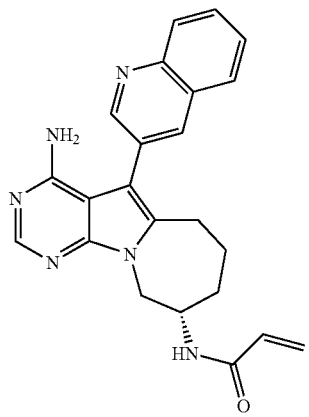 [SMILES: C=CC(=O)N[C@H]1CCCc2c(-c3cnc4ccccc4c3)c3c(N)ncnc3n2C1]

The same procedure as in Reference Example 13 was repeated using (S)-tert-butyl(4-amino-5-(quinolin-3-yl)-7,8,9,10-tetrahydro-6H-pyrimido[5',4':4,5]pyrrolo[1,2-a]azepin-9-yl)carbamate obtained in the below-described Example 14, thereby giving 400.0 mg of the title compound as a milky white solid.

$^1$H-NMR (DMSO-$d_6$) δ: 1.57-1.65 (1H, m), 1.78-1.86 (1H, m), 1.93-2.05 (2H, m), 2.77-2.89 (2H, m), 3.98-4.04 (1H, m), 4.21-4.26 (1H, m), 4.63 (1H, d, J=13.7 Hz), 5.60 (1H, dd, J=10.0, 2.4 Hz), 5.93 (1H, brs), 6.12 (1H, dd, J=17.1, 2.4 Hz), 6.25 (1H, dd, J=17.1-10.0 Hz), 7.63-7.67 (1H, m), 7.77-7.81 (1H, m), 8.07 (1H, t, J=8.8 Hz), 8.12 (1H, s), 8.15 (1H, d, J=7.6 Hz), 8.28 (1H, d, J=2.2 Hz), 8.87 (1H, d, J=2.2 Hz).

ESI-MS m/z 399 (MH+).

Reference Example 15

Synthesis of (S,E)-N-(4-amino-5-(quinolin-3-yl)-6,7,8,9-tetrahydropyrimido[5,4-b]indolizin-8-yl)-3-chloroacrylamide

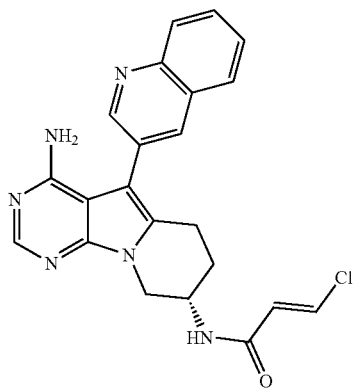 [SMILES: Nc1ncnc2c1c(-c1cnc3ccccc3c1)c1n2C[C@@H](NC(=O)/C=C/Cl)CC1]

Step 1

Synthesis of (S)-5-(quinolin-3-yl)-6,7,8,9-tetrahydropyrimido[5,4-b]indolizine-4,8-diamine

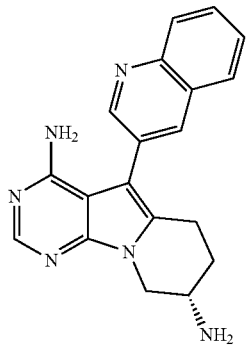 [SMILES: Nc1ncnc2c1c(-c1cnc3ccccc3c1)c1n2C[C@@H](N)CC1]

Hydrochloric acid (4 mol/l, 1,4-dioxane solution, 26 ml) was added at room temperature to (S)-tert-butyl(4-amino-5-(quinolin-3-yl)-6,7,8,9-tetrahydropyrimido[5,4-b]indolizin-8-yl)carbamate (2.6 g) obtained in the below-described Example 1, and the mixture was stirred for 1 hour. After the reaction mixture was subjected to distillation under reduced pressure, the obtained residue was purified by NH silica gel column chromatography (developing solvent: chloroform/methanol), thereby giving 1.72 g of the title compound as a pale yellow solid.

ESI-MS m/z 331 (MH+).

Step 2

Synthesis of (S,E)-N-(4-amino-5-(quinolin-3-yl)-6,7,8,9-tetrahydropyrimido[5,4-b]indolizin-8-yl)-3-chloroacrylamide Trans-3-chloroacrylic acid (399.5 mg) was added at room temperature to a suspension of the (S)-5-(quinolin-3-yl)-6,7,8,9-tetrahydropyrimido[5,4-b]indolizine-4,8-diamine (498.0 mg) obtained in Step 1 in DMF (8 ml). After dissolution, 1-(3-dimethylaminopropyl)-3-ethylcarbodiimide hydrochloride salt (350.1 mg) was added thereto with ice-cooling, and the mixture was stirred at the same temperature for 1 hour. The reaction mixture was poured into a saturated sodium bicarbonate aqueous solution, followed by extraction with ethyl acetate. The organic layer was dried over anhydrous sodium sulfate, and the solvent was distilled off under reduced pressure. The obtained residue was purified by silica gel column chromatography (developing solvent: ethyl acetate/methanol), thereby giving 261.2 mg of the title compound as a pale yellow solid.

$^1$H-NMR (DMSO-$d_6$) δ: 1.84-2.07 (2H, m), 2.92-3.08 (2H, m), 3.88-4.02 (1H, m), 4.27-4.43 (2H, m), 6.07 (2H, brs), 6.48 (1H, d, J=13.4 Hz), 7.31 (1H, d, J=13.2 Hz), 7.63 (1H, t, J=7.4 Hz), 7.75 (1H, t, J=7.6 Hz), 8.03 (1H, d, J=10.7 Hz), 8.05 (1H, d, J=10.7 Hz), 8.13 (1H, s), 8.29 (1H, d, J=2.0H z), 8.53 (1H, d, J=6.6 Hz), 8.92 (1H, d, J=2.2 Hz).

ESI-MS m/z 419, 421 (MH+).

Reference Example 16

Synthesis of (S,Z)-N-(4-amino-5-(quinolin-3-yl)-6,7,8,9-tetrahydropyrimido[5,4-b]indolizin-8-yl)-3-chloroacrylamide

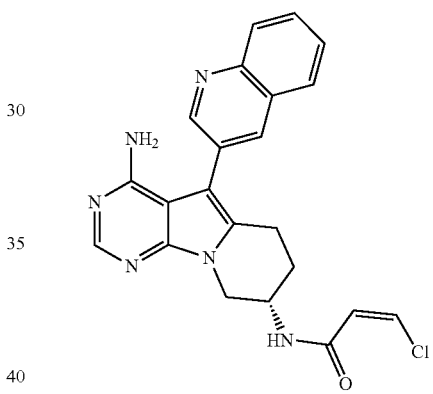

The same procedure as in Reference Example 15 was repeated using cis-3-chloroacrylic acid in place of the trans-3-chloroacrylic acid used in Reference Example 15, thereby giving 93 mg of the title compound as a pale yellow solid.

$^1$H-NMR (DMSO-$d_6$) δ: 1.82-1.96 (1H, m), 1.96-2.07 (1H, m), 2.92-3.08 (2H, m), 3.85-3.97 (1H, m), 4.27-4.41 (2H, m), 6.05 (2H, brs), 6.39 (1H, d, J=8.0 Hz), 6.77 (1H, d, J=8.0 Hz), 7.63 (1H, t, J=7.4 Hz), 7.75 (1H, t, J=7.4 Hz), 8.02 (1H, d, J=11.4 Hz), 8.04 (1H, d, J=11.4 Hz), 8.13 (1H, s), 8.29 (1H, d, J=2.0 Hz), 8.50 (1H, d, J=6.3 Hz), 8.92 (1H, d, J=2.0 Hz).

ESI-MS m/z 419, 421 (MH+).

Reference Example 17

Measurement of Inhibitory Activity Against Various EGFR Kinase Activities (In Vitro)

The compounds prepared in Reference Examples 13 to 16 were evaluated using the following test method.
1) Measurement of EGFR (T790M/L858R) Kinase Inhibitory Activity The inhibitory activity of the compounds prepared in Reference Examples 13 to 16 against EGFR (T790M/L858R) kinase activity was measured.

The materials were provided as follows. For a substrate peptide, a biotinylated amino acid (biotin-EEPLYWSF-PAKKK) (SEQ ID NO: 1) was synthesized with reference to FL-Peptide 22, a series reagent of LabChip (registered trademark), of Caliper Life Sciences, Inc. For EGFR (T790M/L858R), a purified recombinant human EGFR (T790M/L858R) protein of Carna Biosciences, Inc. was purchased.

The measuring procedure is as follows. The compounds prepared in Reference Examples 13 to 16 were individually diluted with dimethyl sulfoxide (DMSO) in stages. Subsequently, the EGFR (T790M/L858R) protein, the substrate peptide (final concentration: 250 nM), magnesium chloride (final concentration: 10 mM), manganese chloride (final concentration: 10 mM), ATP (final concentration: 1 μM), and each DMSO solution of the compound (final concentration of DMSO: 2.5%) were added to a buffer solution for the kinase reaction (Carna Biosciences, Inc.). The mixtures were incubated at 25° C. for 120 minutes to carry out a kinase reaction. EDTA was then added thereto such that the final concentration became 24 mM, thereby terminating the reaction. A detection liquid containing europium (Eu)-labeling anti-phosphorylated tyrosine antibody PT66 (PerkinElmer, Inc.) and SureLight APC-SA (PerkinElmer, Inc.) was added to each of the reaction mixtures, and the mixtures were allowed to stand at room temperature for 2 hours or more. Finally, the amount of fluorescence at the time of irradiation of excitation light having a wavelength of 337 nm was measured at dual wavelengths of 620 nm and 665 nm by PHERAstar FS (BMG LABTECH). The amount of phosphorylation was determined from the ratio of the fluorescence amounts at the dual wavelengths, and the $IC_{50}$ value (nM), which is a compound concentration at which phosphorylation can be inhibited by 50%, was determined.

2) Measurement of EGFR (d746-750/T790M) Kinase Inhibitory Activity

The inhibitory activity of the compounds prepared in Reference Examples 13 to 16 against EGFR (d746-750/T790M) kinase activity was measured.

The materials were provided as follows. For EGFR (d746-750/T790M), a purified recombinant human EGFR (d746-750/T790M) protein of Carna Biosciences, Inc. was purchased. The final concentration of ATP was 1.5 μM. In addition, using the same materials and the same measuring method used in the measurement of EGFR (T790M/L858R) kinase inhibitory activity, the $IC_{50}$ value (nM) was determined.

3) Measurement of EGFR (L858R) Kinase Inhibitory Activity

The inhibitory activity of the compounds prepared in Reference Examples 13 to 16 against EGFR (L858R) kinase activity was measured.

The materials were provided as follows. For EGFR (L858R), a purified recombinant human EGFR (L858R) protein of Carna Biosciences, Inc. was purchased. The final concentration of ATP was 4 μM. In addition, using the same materials and the same measuring method used in the measurement of EGFR (T790M/L858R) kinase inhibitory activity, the $IC_{50}$ value (nM) was determined.

4) Measurement of EGFR (d746-750) Kinase Inhibitory Activity

The inhibitory activity of the compounds prepared in Reference Examples 13 to 16 against EGFR (d746-750) kinase activity was measured.

The materials were provided as follows. For EGFR (d746-750), a purified recombinant human EGFR (d746-750) protein of Carna Biosciences, Inc. was purchased. The final concentration of ATP was 5 μM. The incubation for a kinase reaction was carried out for 90 minutes. In addition, using the same materials and the same measuring method used in the measurement of EGFR (T790M/L858R) kinase inhibitory activity, the $IC_{50}$ value (nM) was determined.

5) EGFR (WT)

The inhibitory activity of the compounds prepared in Reference Examples 13 to 16 against EGFR (WT) kinase activity was measured.

The materials were provided as follows. For EGFR (WT), a human EGFR (WT) intracytoplasmic domain having a FLAG tag fused to its N-terminus was expressed in the insect cell Sf9 using a baculovirus expression system, and purified using anti-FLAG antibody agarose (Sigma-Aldrich Co. LLC) for use. The final concentration of the substrate peptide was 500 nM, and the final concentration of ATP was 4.7 μM. In addition, using the same materials and the same measuring method used in the measurement of EGFR (T790M/L858R) kinase inhibitory activity, the $IC_{50}$ value (nM) was determined.

Table 1 shows the results.

The compounds prepared in Reference Examples 13 to 16 exhibited potent inhibitory activity against not only EGFR (L858R) and EGFR (d746-750), but also EGFR (T790M/L858R) and EGFR (d746-750/T790M). In contrast, the compounds exhibited weak inhibitory activity against EGFR (WT).

TABLE 1

| | EGFR (T790M/L858R) | EGFR (d746-750/T790M) | EGFR (L858R) | EGFR (d746-750) | EGFR (WT) |
|---|---|---|---|---|---|
| Compound of Reference Example 13 | 1.4 | 0.5 | 2.9 | 1.8 | 33 |
| Compound of Reference Example 14 | 18 | 13 | 41 | 20 | 490 |
| Compound of Reference Example 15 | 0.4 | 0.3 | 0.7 | 0.5 | 5.9 |
| Compound of Reference Example 16 | 1.2 | 1.2 | 2.9 | 3.6 | 41 |

Example 1

Synthesis of (S)-tert-butyl(4-amino-5-(quinolin-3-yl)-6,7,8,9-tetrahydropyrimido[5,4-b]indolizin-8-yl)carbamate

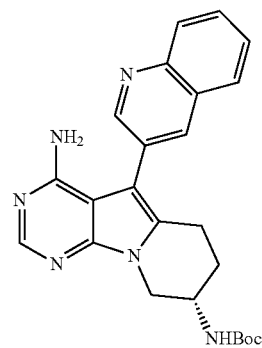 [SMILES: CC(C)(C)OC(=O)N[C@H]1CCc2c(-c3cnc4ccccc4c3)c3c(N)ncnc3n2C1]

A solution of 9-borabicyclo[3.3.1]nonane in 0.5 M tetrahydrofuran (141.3 ml) was added to a solution of the (S)-tert-butyl(1-(4-amino-6-bromo-5-(quinolin-3-yl)-7H-pyrrolo[2,3-d]pyrimidin-7-yl)but-3-en-2-yl)carbamate (6.0 g) obtained in Reference Example 1 in tetrahydrofuran (42 ml) in a nitrogen atmosphere at room temperature, and the mixture was stirred at room temperature for 2 hours. After a 2N aqueous sodium hydroxide solution (84.8 ml) was slowly added at room temperature to the reaction mixture, the mixture was degassed under reduced pressure, and tetrakis(triphenylphosphine)palladium(0) (1.70 g) was added thereto in a nitrogen atmosphere, followed by stirring at 66° C. for 12 hours. After the reaction mixture was cooled, the organic layer was separated, and washed with a 20% aqueous ammonium chloride solution (60 ml). SH silica gel (6.0 g) was added to the organic layer, and the mixture was stirred at 50° C. in a nitrogen atmosphere for 14 hours, followed by filtration. SH silica gel (Fuji Silysia Chemical Ltd., 6.0 g) was again added to the filtrate, and the mixture was stirred at 50° C. in a nitrogen atmosphere for 14 hours, followed by filtration. The solvent was distilled off from the filtrate under reduced pressure. The obtained residue was purified by silica gel column chromatography (developing solvent: ethyl acetate/methanol), thereby giving 4.46 g of the title compound as a pale yellow solid (yield: 88%).

$^1$H-NMR (CDCl$_3$) δ: 1.48 (9H, s), 1.91-2.00 (1H, m), 2.12-2.19 (1H, m), 2.98-3.11 (2H, m), 4.00 (1H, dd, J=12.7, 7.1 Hz), 4.32 (1H, brs), 4.55 (1H, dd, J=12.7, 4.6 Hz), 4.81-4.83 (1H, m), 4.90 (2H, brs), 7.61-7.65 (1H, m), 7.75-7.80 (1H, m), 7.88 (1H, d, J=8.0 Hz), 8.16-8.18 (2H, m), 8.33 (1H, s), 9.02 (1H, d, J=2.2 Hz).

ESI-MS m/z 431 (MH+)

Example 2

Synthesis of (S)-tert-butyl(4-amino-5-(quinolin-3-yl)-6,7,8,9-tetrahydropyrimido[5,4-b]indolizin-8-yl)carbamate 9-borabicyclo[3.3.1]nonane dimer (0.431 g) was added to a solution of the (S)-tert-butyl(1-(4-amino-6-bromo-5-(quinolin-3-yl)-7H-pyrrolo[2,3-d]pyrimidin-7-yl)but-3-en-2-yl)carbamate (0.3 g) obtained in Reference Example 1 in tetrahydrofuran (4.5 ml) at room temperature in a nitrogen atmosphere, and the mixture was stirred at room temperature for 2 hours. A 4N aqueous sodium hydroxide solution (2.12 ml) was slowly added to the reaction mixture at room temperature, and the mixture was degassed under reduced pressure. Tetrakis(triphenylphosphine)palladium(0) (0.136 g) was added thereto in a nitrogen atmosphere, and the mixture was stirred at 64° C. for 12 hours. After cooling, the reaction mixture was diluted with ethyl acetate, and a saturated aqueous ammonium chloride solution was added thereto. At this stage, the generated insoluble substances were removed by filtration, and the organic layer was separated. The obtained organic layer was dried over anhydrous sodium sulfate, filtered, and concentrated under reduced pressure, thereby giving a crude product. This product was purified by silica gel column chromatography (developing solvent: ethyl acetate/methanol), thereby giving 203 mg of (S)-tert-butyl(4-amino-5-(quinolin-3-yl)-6,7,8,9-tetrahydropyrimido[5,4-b]indolizin-8-yl)carbamate as a pale yellow solid (yield: 80%).

Example 3

Synthesis of (S)-tert-butyl(4-amino-5-(quinolin-3-yl)-6,7,8,9-tetrahydropyrimido[5,4-b]indolizin-8-yl)carbamate 9-borabicyclo[3.3.1]nonane dimer (431 mg) was added to a solution of the (S)-tert-butyl(1-(4-amino-6-bromo-5-(quinolin-3-yl)-7H-pyrrolo[2,3-d]pyrimidin-7-yl)but-3-en-2-yl)carbamate (300 mg) obtained in Reference Example 1 in 1,2-dimethoxyethane (4.5 ml) in a nitrogen atmosphere at room temperature, and the mixture was stirred at 48° C. for 40 minutes. After the reaction mixture was allowed to stand at room temperature, a 4N aqueous sodium hydroxide solution (2.1 ml) was slowly added thereto at room temperature, and the mixture was degassed under reduced pressure. Tetrakis(triphenylphosphine)palladium(0) (136 mg) was added thereto in a nitrogen atmosphere, and the mixture was stirred at 79° C. for 5 hours. After cooling, the reaction mixture was diluted with ethyl acetate, and a saturated aqueous ammonium chloride solution was added thereto. At this stage, the generated insoluble substances were removed by filtration, and the organic layer was separated. The obtained organic layer was dried over anhydrous sodium sulfate, filtered, and concentrated under reduced pressure, thereby giving a crude product. This product was purified by silica gel column chromatography (developing solvent: ethyl acetate/methanol), thereby giving 0.190 g of (S)-tert-butyl(4-amino-5-(quinolin-3-yl)-6,7,8,9-tetrahydropyrimido[5,4-b]indolizin-8-yl)carbamate as a pale yellow solid (yield: 75%).

Example 4

Synthesis of (S)-tert-butyl(4-amino-5-(quinolin-3-yl)-6,7,8,9-tetrahydropyrimido[5,4-b]indolizin-8-yl)carbamate The same procedure as in Example 1 was repeated using a 4N aqueous lithium hydroxide solution (1.8 ml) in place of the aqueous sodium hydroxide solution in Example 1, thereby giving 224 mg of (S)-tert-butyl(4-amino-5-(quinolin-3-yl)-6,7,8,9-tetrahydropyrimido[5,4-b]indolizin-8-yl)carbamate as a pale yellow solid (yield: 88%).

Example 5

Synthesis of (S)-tert-butyl(4-amino-5-(quinolin-3-yl)-6,7,8,9-tetrahydropyrimido[5,4-b]indolizin-8-yl)carbamate The same procedure as in Example 1 was repeated using a 4N aqueous potassium hydroxide solution (1.8 ml) in place of the aqueous sodium hydroxide solution in Example 1, thereby giving 198 mg of (S)-tert-butyl(4-amino-5-(quinolin-3-yl)-6,7,8,9-tetrahydropyrimido[5,4-b]indolizin-8-yl)carbamate as a pale yellow solid (yield: 78%).

Example 6

Synthesis of (S)-tert-butyl(4-amino-5-(quinolin-3-yl)-6,7,8,9-tetrahydropyrimido[5,4-b]indolizin-8-yl)carbamate The same procedure as in Example 1 was repeated using a 4N aqueous cesium hydroxide solution (1.8 ml) in place of the aqueous sodium hydroxide solution in Example 1, thereby giving 202 mg of (S)-tert-butyl(4-amino-5-(quinolin-3-yl)-6,7,8,9-tetrahydropyrimido[5,4-b]indolizin-8-yl)carbamate as a pale yellow solid (yield: 80%).

Example 7

Synthesis of (S)-tert-butyl(4-amino-5-(quinolin-3-yl)-6,7,8,9-tetrahydropyrimido[5,4-b]indolizin-8-yl)carbamate The same procedure as in Example 1 was repeated using tris(dibenzylideneacetone)dipalladium(0) (34 mg) and triphenylphosphine (39 mg) in place of the tetrakis(triphenylphosphine)palladium(0) in Example 1, thereby giving 194 mg of (S)-tert-butyl(4-amino-5-(quinolin-3-yl)-6,7,8,9-tetrahydropyrimido[5,4-b]indolizin-8-yl)carbamate as a pale yellow solid (yield: 76%).

Example 8

Synthesis of (R)-tert-butyl(4-amino-5-(quinolin-3-yl)-6,7,8,9-tetrahydropyrimido[5,4-b]indolizin-8-yl)carbamate

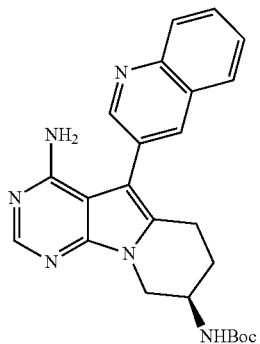 [SMILES: CC(C)(C)OC(=O)N[C@@H]1CCc2c(-c3cnc4ccccc4c3)c3c(N)ncnc3n2C1]

The same procedure as in Example 1 was repeated using 6.70 g of the (R)-tert-butyl(1-(4-amino-6-bromo-5-(quinolin-3-yl)-7H-pyrrolo[2,3-d]pyrimidin-7-yl)but-3-en-2-yl)carbamate obtained in Reference Example 2 in place of the (S)-tert-butyl(1-(4-amino-6-bromo-5-(quinolin-3-yl)-7H-pyrrolo[2,3-d]pyrimidin-7-yl)but-3-en-2-yl)carbamate in Example 1, thereby giving 4.76 g of (R)-tert-butyl(4-amino-5-(quinolin-3-yl)-6,7,8,9-tetrahydropyrimido[5,4-b]indolizin-8-yl)carbamate as a pale yellow solid (yield: 84%).

$^1$H-NMR (CDCl$_3$) δ: 1.48 (9H, s), 1.91-2.00 (1H, m), 2.12-2.19 (1H, m), 2.98-3.11 (2H, m), 4.00 (1H, dd, J=12.7, 7.1 Hz), 4.32 (1H, brs), 4.55 (1H, dd, J=12.7, 4.6 Hz), 4.81-4.83 (1H, m), 4.90 (2H, brs), 7.61-7.65 (1H, m), 7.75-7.80 (1H, m), 7.88 (1H, d, J=8.0 Hz), 8.16-8.18 (2H, m), 8.33 (1H, s), 9.02 (1H, d, J=2.2 Hz).

ESI-MS m/z 431 (MH+)

Example 9

Synthesis of (S)-tert-butyl(4-amino-6,7,8,9-tetrahydropyrimido[5,4-b]indolizin-8-yl)carbamate

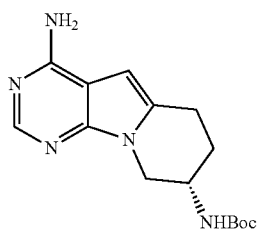 [SMILES: CC(C)(C)OC(=O)N[C@H]1CCc2cc3c(N)ncnc3n2C1]

The same procedure as in Example 1 was repeated using 2.84 g of the (S)-tert-butyl(1-(4-amino-6-bromo-7H-pyrrolo[2,3-d]pyrimidin-7-yl)but-3-en-2-yl)carbamate obtained in Reference Example 3 in place of (S)-tert-butyl(1-(4-amino-6-bromo-5-(quinolin-3-yl)-7H-pyrrolo[2,3-d]pyrimidin-7-yl)but-3-en-2-yl)carbamate, thereby giving 1.10 g of (S)-tert-butyl(4-amino-6,7,8,9-tetrahydropyrimido[5,4-b]indolizin-8-yl)carbamate as a pale yellow solid (yield: 49%).

$^1$H-NMR (DMSO-d$_6$) δ: 1.38 (s, 9H), 1.62-1.81 (m, 1H), 1.89-2.02 (m, 1H), 2.73-2.89 (m, 1H), 2.91-3.06 (m, 1H), 3.60 (dd, J=12.30-8.88 Hz, 1H), 3.79-3.93 (m, 1H), 4.23 (dd, J=12.30, 4.78 Hz, 1H), 6.17 (s, 1H), 6.74 (brs, 2H), 7.16 (d, J=6.15 Hz, 1H), 7.94 (s, 1H).

ESI-MS m/z 304 (MH+)

Example 10

Synthesis of (R)-tert-butyl(4-amino-6,7,8,9-tetrahydropyrimido[5,4-b]indolizin-8-yl)carbamate

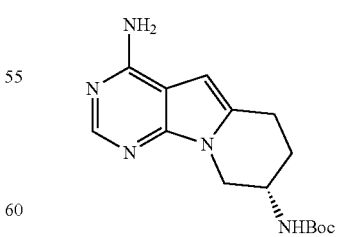

The same procedure as in Example 1 was repeated using 0.9 g of the (R)-tert-butyl(1-(4-amino-6-bromo-7H-pyrrolo[2,3-d]pyrimidin-7-yl)but-3-en-2-yl)carbamate obtained in Reference Example 4 in place of the (S)-tert-butyl(1-(4-amino-6-bromo-5-(quinolin-3-yl)-7H-pyrrolo[2,3-d]pyrimidin-7-yl)but-3-en-2-yl)carbamate in Example 1, thereby giving 0.54 g of (R)-tert-butyl(4-amino-6,7,8,9-tetrahydropyrimido[5,4-b]indolizin-8-yl)carbamate as a pale yellow solid (yield: 76%).

$^1$H-NMR (DMSO-d$_6$) δ: 1.38 (s, 9H), 1.62-1.81 (m, 1H), 1.89-2.02 (m, 1H), 2.73-2.89 (m, 1H), 2.91-3.06 (m, 1H), 3.60 (dd, J=12.30-8.88 Hz, 1H), 3.79-3.93 (m, 1H), 4.23 (dd, J=12.30, 4.78 Hz, 1H), 6.17 (s, 1H), 6.74 (brs, 2H), 7.16 (d, J=6.15 Hz, 1H), 7.94 (s, 1H).

ESI-MS m/z 304 (MH+)

Example 11

Synthesis of (S)-tert-butyl(4-amino-6,7,8,9-tetrahydropyrimido[5,4-b]indolizin-8-yl)carbamate The same procedure as in Example 1 was repeated using 1.0 g of the (S)-tert-butyl(1-(4-amino-6-iodo-7H-pyrrolo[2,3-d]pyrimidin-7-yl)but-3-en-2-yl)carbamate obtained in Reference Example 5 in place of (S)-tert-butyl(1-(4-amino-6-bromo-5-(quinolin-3-yl)-7H-pyrrolo[2,3-d]pyrimidin-7- yl)but-3-en-2-yl)carbamate, thereby giving 0.48 g of (S)-tert-butyl(4-amino-6,7,8,9-tetrahydropyrimido[5,4-b]indolizin-8-yl)carbamate as a pale yellow solid (yield: 68%).

¹H-NMR (DMSO-d₆) δ: 1.38 (s, 9H), 1.62-1.81 (m, 1H), 1.89-2.02 (m, 1H), 2.73-2.89 (m, 1H), 2.91-3.06 (m, 1H), 3.60 (dd, J=12.30-8.88 Hz, 1H), 3.79-3.93 (m, 1H), 4.23 (dd, J=12.30, 4.78 Hz, 1H), 6.17 (s, 1H) 6.74 (brs, 2H), 7.16 (d, J=6.15 Hz, 1H), 7.94 (s, 1H).

ESI-MS m/z 304 (MH+)

Example 12

Synthesis of (S)-tert-butyl(4-amino-5-cyclopropyl-6,7,8,9-tetrahydropyrimido[5,4-b]indolizin-8-yl)carbamate

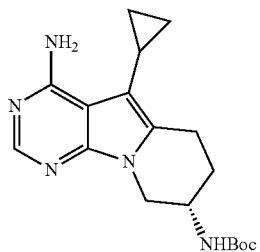 [SMILES: CC(C)(C)OC(=O)N[C@H]1CCc2c(C3CC3)c3c(N)ncnc3n2C1]

The same procedure as in Example 1 was repeated using 270.0 mg of the (S)-tert-butyl(1-(4-amino-6-bromo-5-cyclopropyl-7H-pyrrolo[2,3-d]pyrimidin-7-yl)but-3-en-2-yl)carbamate obtained in Reference Example 6 in place of the (S)-tert-butyl(1-(4-amino-6-bromo-5-(quinolin-3-yl)-7H-pyrrolo[2,3-d]pyrimidin-7-yl)but-3-en-2-yl)carbamate in Example 1, thereby giving 112.7 mg of the title compound as a pale yellow solid (yield: 51%).

¹H-NMR (CDCl₃) δ: 0.60-0.71 (2H, m), 0.90-1.00 (2H, m), 1.46 (9H, s), 1.50-2.15 (3H, m), 2.84-3.10 (2H, m), 3.85 (1H, dd, J=12.2, 6.8 Hz), 4.20 (1H, brs), 4.36 (1H, dd, J=12.2, 4.8 Hz), 4.72 (1H, brs), 5.59 (2H, brs), 8.20 (1H, s).

ESI-MS m/z 344 (MH+)

Example 13

Synthesis of (S)-tert-butyl(4-amino-5-phenyl-6,7,8,9-tetrahydropyrimido[5,4-b]indolizin-8-yl)carbamate

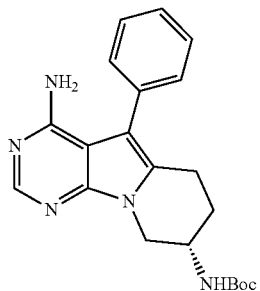 [SMILES: CC(C)(C)OC(=O)N[C@H]1CCc2c(-c3ccccc3)c3c(N)ncnc3n2C1]

The same procedure as in Example 1 was repeated using 1.57 g of the (S)-tert-butyl(1-(4-amino-6-bromo-5-phenyl-7H-pyrrolo[2,3-d]pyrimidin-7-yl)but-3-en-2-yl)carbamate obtained in Reference Example 7 in place of the (S)-tert-butyl(1-(4-amino-6-bromo-5-(quinolin-3-yl)-7H-pyrrolo[2,3-d]pyrimidin-7-yl)but-3-en-2-yl)carbamate in Example 1, thereby giving 922 mg of the title compound as a pale yellow solid (yield: 71%).

¹H-NMR (CDCl₃) δ: 1.47 (9H, s), 1.83-1.96 (1H, m), 2.07-2.15 (1H, m), 2.92-3.05 (2H, m), 3.96 (1H, dd, J=12.6, 7.2 Hz) 4.23-4.35 (1H, m), 4.50 (1H, dd, J=12.6, 4.8 Hz), 4.72-4.82 (1H, m), 4.91-5.05 (2H, m), 7.34-7.41 (3H, m), 7.45-7.49 (2H, m), 8.29 (1H, s).

ESI-MS m/z 380 (MH+)

Example 14

Synthesis of (S)-tert-butyl(4-amino-5-(quinolin-3-yl)-7,8,9,10-tetrahydro-6H-pyrimido[5',4':4,5]pyrrolo[1,2-a]azepin-9-yl)carbamate

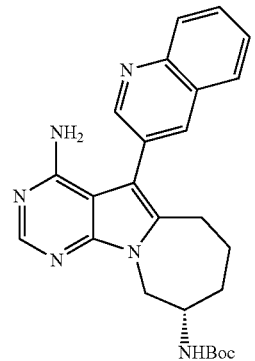 [SMILES: CC(C)(C)OC(=O)N[C@H]1CCCc2c(-c3cnc4ccccc4c3)c3c(N)ncnc3n2C1]

The same procedure as in Example 1 was repeated using 2.0 g of the (S)-tert-butyl(1-(4-amino-6-bromo-5-(quinolin-3-yl)-7H-pyrrolo[2,3-d]pyrimidin-7-yl)pent-4-en-2-yl)carbamate obtained in Reference Example 8 in place of the (S)-tert-butyl(1-(4-amino-6-bromo-5-(quinolin-3-yl)-7H-pyrrolo[2,3-d]pyrimidin-7-yl)but-3-en-2-yl)carbamate in Example 1, thereby giving 1.56 g of the title compound as a pale yellow solid (yield: 92%).

¹H-NMR (CDCl₃) δ: 1.43 (9H, s), 1.77-1.89 (2H, m), 1.95-2.14 (2H, m), 2.71-2.84 (1H, m), 2.86-3.00 (1H, m), 4.00-4.15 (1H, m), 4.24-4.40 (1H, m), 4.40-4.50 (1H, m), 4.84 (3H, brs), 7.62-7.66 (1H, m), 7.77-7.81 (1H, m), 7.89-7.91 (1H, m), 8.18-8.20 (2H, m), 8.33 (1H, s), 8.98 (1H, d, J=1.5 Hz).

ESI-MS m/z 445 (MH+)

Example 15

Synthesis of (R)-tert-butyl(4-amino-5-(quinolin-3-yl)-7,8,9,10-tetrahydro-6H-pyrimido[5',4':4,5]pyrrolo[1,2-a]azepin-9-yl)carbamate

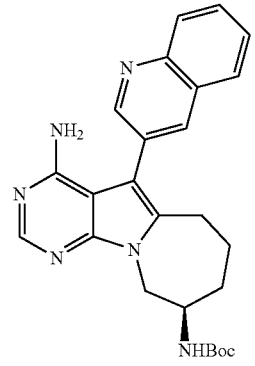 [SMILES: CC(C)(C)OC(=O)N[C@@H]1CCCc2c(-c3cnc4ccccc4c3)c3c(N)ncnc3n2C1]

The same procedure as in Example 1 was repeated using 690 mg of the (R)-tert-butyl(1-(4-amino-6-bromo-5-(quinolin-3-yl)-7H-pyrrolo[2,3-d]pyrimidin-7-yl)pent-4-en-2-yl)carbamate obtained in Reference Example 9 in place of the (S)-tert-butyl(1-(4-amino-6-bromo-5-(quinolin-3-yl)-7H-pyrrolo[2,3-d]pyrimidin-7-yl)but-3-en-2-yl)carbamate in Example 1, thereby giving 429 mg of the title compound as a yellow solid (yield: 73%).

$^1$H-NMR (CDCl$_3$) δ: 1.43 (9H, s), 1.77-1.89 (2H, m), 1.95-2.14 (2H, m), 2.71-2.84 (1H, m), 2.86-3.00 (1H, m), 4.00-4.15 (1H, m), 4.24-4.40 (1H, m), 4.40-4.50 (1H, m), 4.84 (3H, brs), 7.62-7.66 (1H, m), 7.77-7.81 (1H, m), 7.89-7.91 (1H, m), 8.18-8.20 (2H, m), 8.33 (1H, s), 8.98 (1H, d, J=1.5 Hz).

ESI-MS m/z 445 (MH+)

Example 16

Synthesis of (S)-tert-butyl(4-amino-5-(quinolin-3-yl)-7,8,9,10-tetrahydro-6H-pyrimido[5',4':4,5]pyrrolo[1,2-a]azepin-8-yl)carbamate

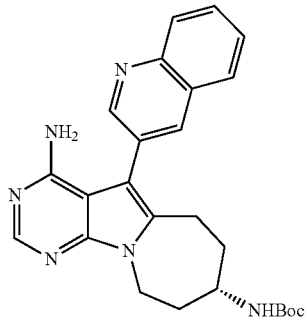 [SMILES: CC(C)(C)OC(=O)N[C@H]1CCc2c(-c3cnc4ccccc4c3)c3c(N)ncnc3n2CC1]

The same procedure as in Example 1 was repeated using 994 mg of the (R)-tert-butyl(5-(4-amino-6-bromo-5-(quinolin-3-yl)-7H-pyrrolo[2,3-d]pyrimidin-7-yl)pent-1-en-3-yl)carbamate obtained in Reference Example 10 in place of the (S)-tert-butyl(1-(4-amino-6-bromo-5-(quinolin-3-yl)-7H-pyrrolo[2,3-d]pyrimidin-7-yl)but-3-en-2-yl)carbamate in Example 1, thereby giving 439 mg of the title compound as a yellow solid (yield: 52%).

$^1$H-NMR (CDCl$_3$) δ: 1.46 (9H, s), 2.18-2.28 (1H, m), 2.32-2.42 (1H, m), 2.65-2.77 (1H, m), 2.99-3.08 (1H, m), 3.80-3.97 (2H, m), 4.53-4.62 (1H, m), 4.80 (2H, brs), 4.97-5.11 (1H, m), 7.61-7.66 (1H, m), 7.76-7.81 (1H, m), 7.88 (1H, d, J=8.0 Hz), 8.15-8.20 (2H, m), 8.33 (1H, s), 8.97 (1H, d, J=2.2 Hz).

ESI-MS m/z 445 (MH+)

Example 17

Synthesis of (R)-8-((tert-butyldimethylsilyl)oxy)-5-(quinolin-3-yl)-6,7,8,9-tetrahydropyrimido[5,4-b]indolizin-4-amine

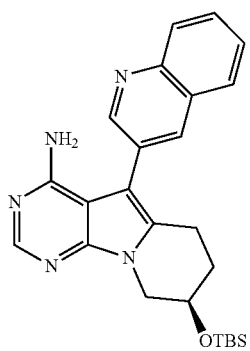 [SMILES: CC(C)(C)[Si](C)(C)O[C@@H]1CCc2c(-c3cnc4ccccc4c3)c3c(N)ncnc3n2C1]

The same procedure as in Example 1 was repeated using 1.0 g of the (R)-6-bromo-7-(2-((tert-butyldimethylsilyl)oxy)but-3-en-1-yl)-5-(quinolin-3-yl)-7H-pyrrolo[2,3-d]pyrimidin-4-amine obtained in Reference Example 11 in place of the (S)-tert-butyl(1-(4-amino-6-bromo-5-(quinolin-3-yl)-7H-pyrrolo[2,3-d]pyrimidin-7-yl)but-3-en-2-yl)carbamate in Example 1, thereby giving 546 mg of (R)-8-((tert-butyldimethylsilyl)oxy)-5-(quinolin-3-yl)-6,7,8,9-tetrahydropyrimido[5,4-b]indolizin-4-amine (yield: 64%).

$^1$H-NMR (CDCl$_3$) δ: 0.14 (3H, s), 0.15 (3H, s), 0.91 (9H, s), 1.97-2.02 (2H, m), 2.85-2.92 (2H, m), 3.14-3.22 (1H, m), 4.11-4.18 (1H, m), 4.28-4.33 (1H, m), 4.41-4.46 (1H, m), 4.95 (2H, brs), 7.61-7.65 (1H, m), 7.75-7.79 (1H, m), 7.88-7.90 (1H, m), 8.16-8.18 (2H, m), 8.35 (1H, s), 9.04 (1H, d, J=2.0 Hz).

ESI-MS m/z 446 (MH+)

Example 18

Synthesis of (R)-tert-butyl(4-amino-5-(quinolin-3-yl)-6,7,8,9-tetrahydropyrimido[5,4-b]indolizin-8-yl)(methyl)carbamate

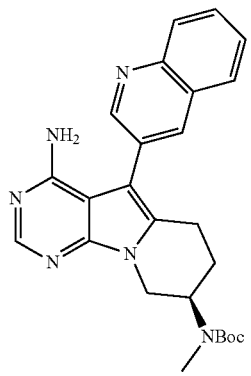 [SMILES: CN(C(=O)OC(C)(C)C)[C@@H]1CCc2c(-c3cnc4ccccc4c3)c3c(N)ncnc3n2C1]

The same procedure as in Example 1 was repeated using 800 mg of the (R)-tert-butyl(1-(4-amino-6-bromo-5-(quinolin-3-yl)-7H-pyrrolo[2,3-d]pyrimidin-7-yl)but-3-en-2-yl)(methyl)carbamate obtained in Reference Example 12 in place of the (S)-tert-butyl(1-(4-amino-6-bromo-5-(quinolin-3-yl)-7H-pyrrolo[2,3-d]pyrimidin-7-yl)but-3-en-2-yl)carbamate in Example 1, thereby giving 432 mg of (R)-tert-butyl(4-amino-5-(quinolin-3-yl)-6,7,8,9-tetrahydropyrimido[5,4-b]indolizin-8-yl)(methyl)carbamate as a pale brown solid (yield: 64%).

$^1$H-NMR (CDCl$_3$) δ: 1.51 (9H, s), 1.94-2.18 (2H, m), 1.95-2.18 (2H, m), 2.83-2.93 (1H, m), 2.88 (3H, s), 3.01-3.15 (2H, m), 3.91 (1H, t, J=11.4 Hz), 4.54-4.64 (1H, m), 4.86 (2H, brs), 7.62 (1H, t, J=6.8 Hz), 7.77 (1H, t, J=6.8 Hz), 7.88 (1H, d, J=8.0 Hz), 8.16 (2H, s), 8.34 (1H, s), 9.02 (1H, d, J=2.4 Hz).

ESI-MS m/z 445 (MH+)

Comparative Example 1

Production Method Using Divalent Palladium Catalyst

The compound of Example 1 was produced in accordance with the procedure disclosed in International Publication WO 2006/102079 (pamphlet). Specifically, the same procedure as in Example 1 was repeated using 1,1'-bis(diphenylphosphino)ferrocene palladium(II) dichloride (32 mg) in place of the tetrakis(triphenylphosphine)palladium(0) in Example 1, thereby giving 21 mg of the compound of Example 1 as a pale yellow solid (yield: 25%).

Comparative Example 2

Production Method Using Cesium Carbonate

The compound of Example 1 was produced in accordance with the procedure disclosed in Synthesis (2010, No. 127, 2092-2100). Specifically, the same procedure as in Example 1 was repeated using cesium carbonate (2.3 g) and water (1.8 ml) in place of the aqueous sodium hydroxide solution in Example 1, thereby giving 88 mg of the compound of Example 1 as a pale yellow solid (yield: 35%).

The above results confirm that the production method of the present invention produces a pyrrolopyrimidine ring-containing tricyclic compound in high yield with reduced formation of by-products.

The invention claimed is:

1. A method for producing a compound represented by Formula (1)

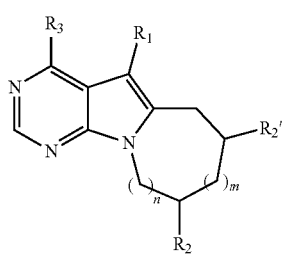

or a salt thereof,
wherein
$R_1$ is hydrogen or a functional group selected from the group consisting of halogen; hydroxy; cyano; nitro; alkyl which may be substituted by $C_{1-6}$ alkoxy, acyl, $C_{2-7}$ alkoxycarbonyl, $C_{1-6}$ alkylamino, 4- to 10-membered saturated heterocycle or 4- to 10-membered unsaturated heterocycle; haloalkyl; cycloalkyl which may be substituted by halogen, $C_{1-6}$ alkyl, $C_{1-6}$ alkoxy, $C_{1-6}$ haloalkyl, acyl, $C_{2-7}$ alkoxycarbonyl, $C_{1-6}$ alkylamino, $C_{3-10}$ cycloalkyl, $C_{6-14}$ aromatic hydrocarbon, 4- to 10-membered saturated heterocycle, or 4- to 10-membered unsaturated heterocycle; cycloalkylalkyl; aralkyl; alkenyl; alkynyl; alkoxy; haloalkoxy; cycloalkoxy; cycloalkyl-alkoxy; aralkyloxy; alkylthio; cycloalkyl-alkylthio; amino; alkylamino; cycloalkylalkylamino; acyl; acyloxy; carboxy; alkoxycarbonyl; aralkyloxycarbonyl; carbamoyl; saturated or unsaturated heterocycle which may be substituted by halogen, $C_{1-6}$ alkyl, $C_{1-6}$ alkoxy, $C_{1-6}$ haloalkyl, acyl, $C_{2-7}$ alkoxycarbonyl, $C_{1-6}$ alkylamino, $C_{3-10}$ cycloalkyl, $C_{6-14}$ aromatic hydrocarbon, 4- to 10-membered saturated heterocycle, or 4- to 10-membered unsaturated heterocycle; aromatic hydrocarbon which may be substituted by halogen, $C_{1-6}$ alkyl, $C_{1-6}$ alkoxy, $C_{1-6}$ haloalkyl, acyl, $C_{2-7}$ alkoxycarbonyl, $C_{1-6}$ alkylamino, $C_{3-10}$ cycloalkyl, $C_{6-14}$ aromatic hydrocarbon, 4- to 10-membered saturated heterocycle, or 4- to 10-membered unsaturated heterocycle; and saturated heterocyclic oxy;

one of $R_2$ and $R_2'$ is
hydroxy protected by a protecting group selected from the group consisting of lower alkylsilyl, lower alkyldiphenylsilyl, lower alkyl lower alkoxyphenylsilyl, and lower alkoxydiphenylsilyl, amino protected by alkoxycarbonyl or $C_{1-6}$ alkylamino protected by alkoxycarbonyl, each of which may be substituted, or thiol protected by a protecting group selected from the group consisting of aralkyl, benzyloxymethyl, benzylthiomethyl, lower alkoxycarbonyl, 2,2,2-trichloroethoxycarbonyl, 9-fluorenylmethoxycarbonyl, tert-butylsulfanyl, and 3-nitro-2-pyridinesulfenyl; wherein said alkyloxycarbonyl is unsubstituted or substituted with a substituent selected from the group consisting of halogen, adamantyl, trimethylsilyl, phenyl, methoxyphenyl, nitrophenyl, anthryl, and fluorenyl;

the other of $R_2$ and $R_2'$ is hydrogen;

$R_3$ is amino which is unsubstituted or substituted with a substituent selected from the group consisting of $C_{1-6}$ alkyl, $C_{1-6}$ haloalkyl, acyl, $C_{2-7}$ alkoxycarbonyl, $C_{1-6}$ alkylamino, $C_{3-10}$ cycloalkyl and 4- to 10-membered saturated heterocycle;

m is 0 or 1; and n or 1 or 2, the method comprising the steps of:

(I) reacting an organoborane with a compound represented by Formula (2)

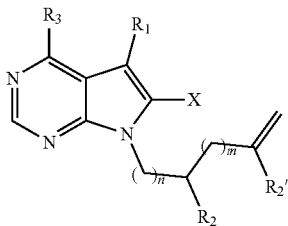

(2)

or a salt thereof,
wherein said organoborane is selected from the group consisting of 9-borabicyclo[3.3.1]nonane, 9-borabicyclo[3.3.1]nonane dimer, bis(1,2-dimethylpropyl)borane and (1,1,2-trimethylpropyl)borane,
wherein X is halogen, and $R_1$, $R_2$, $R_2'$, $R_3$, m, and n are as defined above; and
(II) intramolecularly cyclizing the product obtained in step (I) in the presence of a zerovalent palladium catalyst and an alkali metal hydroxide.

2. The method according to claim 1,
wherein
X is bromo or iodo;
$R_1$ is hydrogen, $C_{1-6}$ alkyl which may be substituted, $C_{3-10}$ cycloalkyl which may be substituted, $C_{6-14}$ aromatic hydrocarbon which may be substituted, 4- to 10-membered saturated heterocycle which may be substituted, or 4- to 10-membered unsaturated heterocycle which may be substituted;
one of $R_2$ and $R_2'$ is hydroxy protected by a protecting group selected from the group consisting of lower alkylsilyl, lower alkyldiphenylsilyl, lower alkyl lower alkoxyphenylsilyl, and lower alkoxydiphenylsilyl, or amino protected by alkoxycarbonyl or $C_{1-6}$ alkylamino protected by alkoxycarbonyl, each of which may be substituted;
the other of $R_2$ and $R_2'$ is hydrogen; and
$R_3$ is amino.

3. The method according to claim 1,
wherein
m is 0 or 1;
n is 1 or 2;
X is bromo or iodo;
$R_1$ is hydrogen, $C_{3-7}$ cycloalkyl, $C_{6-14}$ aromatic hydrocarbon, or 4- to 10-membered unsaturated heterocycle;
one of $R_2$ and $R_2'$ is hydroxy protected by a protecting group selected from the group consisting of lower alkylsilyl, lower alkyldiphenylsilyl, lower alkyl lower alkoxyphenylsilyl, and lower alkoxydiphenylsilyl, or amino protected by alkoxycarbonyl or $C_{1-6}$ alkylamino protected by alkoxycarbonyl, each of which may be substituted;
the other of $R_2$ and $R_2'$ is hydrogen; and
$R_3$ is amino.

4. The method according to claim 1,
wherein
(i) m is 0 and n is 1; (ii) m is 1 and n is 1; or (iii) m is 0 and n is 2;
X is bromo or iodo;
$R_1$ is hydrogen, cyclopropyl, phenyl, or quinolyl;
one of $R_2$ and $R_2'$ is hydroxy protected by tert-butyldimethylsilyl, or amino protected by tert-butoxycarbonyl or $C_{1-4}$ alkylamino protected by tert-butoxycarbonyl;
the other of $R_2$ and $R_2'$ is hydrogen; and
$R_3$ is amino.

5. The method according to claim 1, wherein the zerovalent palladium catalyst is tetrakis(triphenylphosphine)palladium(0) or tris(dibenzylideneacetone)dipalladium(0).

6. The method according to claim 1, wherein the alkali metal hydroxide is lithium hydroxide, sodium hydroxide, potassium hydroxide, or cesium hydroxide.

7. The method according to claim 1, wherein the organoborane is 9-borabicyclo[3.3.1]nonane or 9-borabicyclo[3.3.1]nonane dimer.

* * * * *

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Substrate Peptide For EGFR Kinase; Biotinylated
      at N-terminus

<400> SEQUENCE: 1

Glu Glu Pro Leu Tyr Trp Ser Phe Pro Ala Lys Lys Lys
1               5                   10
```